United States Patent [19]
Swanson et al.

[11] Patent Number: 5,961,513
[45] Date of Patent: Oct. 5, 1999

[54] TISSUE HEATING AND ABLATION SYSTEMS AND METHODS USING POROUS ELECTRODE STRUCTURES

[75] Inventors: David K. Swanson, Mountain View; Dorin Panescu, Sunnyvale; James G. Whayne, Saratoga; Patrick M. Owens, Cupertino; Russell B. Thompson, Los Altos, all of Calif.

[73] Assignee: EP Technologies, Inc., Sunnyvale, Calif.

[21] Appl. No.: 08/631,575

[22] Filed: Apr. 12, 1996

Related U.S. Application Data

[60] Provisional application No. 60/010,223, Jan. 19, 1996, provisional application No. 60/010,225, Jan. 19, 1996, and provisional application No. 60/010,354, Jan. 19, 1996.

[51] Int. Cl.⁶ ................................................. A61B 17/39
[52] U.S. Cl. ............................ 606/34; 606/41; 607/99; 607/105; 607/113; 607/122
[58] Field of Search ................... 606/33, 41, 34; 607/99, 100, 105, 113, 122; 604/21

[56] References Cited

U.S. PATENT DOCUMENTS

| | | |
|---|---|---|
| 4,979,948 | 12/1990 | Geddes et al. .......................... 606/33 |
| 5,117,828 | 6/1992 | Metzger et al. ......................... 607/124 |
| 5,195,969 | 3/1993 | Wang et al. . |
| 5,255,678 | 10/1993 | Deslauriers et al. . |
| 5,277,201 | 1/1994 | Stern . |
| 5,293,869 | 3/1994 | Edwards et al. . |
| 5,311,866 | 5/1994 | Kagan et al. . |
| 5,334,193 | 8/1994 | Nardella . |
| 5,391,200 | 2/1995 | Kenknight et al. . |
| 5,462,545 | 10/1995 | Wang et al. . |
| 5,472,441 | 12/1995 | Edwards et al. . |
| 5,499,971 | 3/1996 | Shapland et al. ........................ 604/21 |
| 5,505,730 | 4/1996 | Edwards . |
| 5,562,720 | 10/1996 | Stern et al. . |
| 5,569,241 | 10/1996 | Edwards . |
| 5,598,848 | 2/1997 | Swanson et al. . |

FOREIGN PATENT DOCUMENTS

| | | |
|---|---|---|
| 0 080 536 | 6/1983 | European Pat. Off. . |
| 3516830 | 11/1986 | Germany . |
| 1220-673 | 3/1986 | Russian Federation . |
| WO95/01751 | 1/1995 | WIPO . |
| WO 96/00041 | 1/1996 | WIPO . |

OTHER PUBLICATIONS

Fann et al., Endocardial Activation Mapping and Endocardial Pace–Mapping Using a Balloon Apparatus, The American Journal of Cardiology, Apr. 1, 1995, pp. 1076–1083.

*Primary Examiner*—Lee Cohen
*Attorney, Agent, or Firm*—Lyon & Lyon LLP

[57] ABSTRACT

Porous electrode assemblies for tissue heating and ablation systems and methods enable ionic transport of electrical energy to occur substantially free of liquid perfusion.

92 Claims, 18 Drawing Sheets

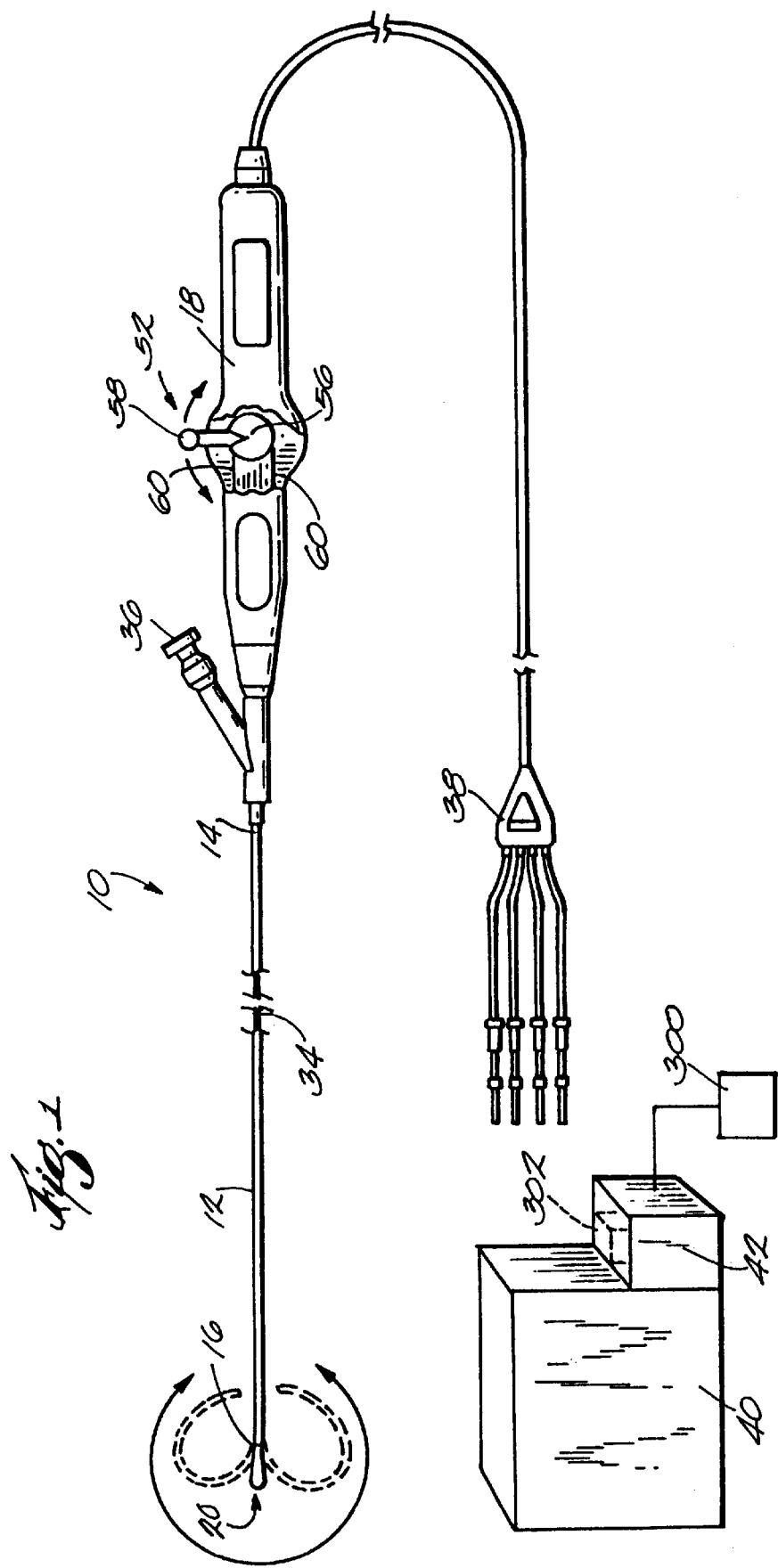

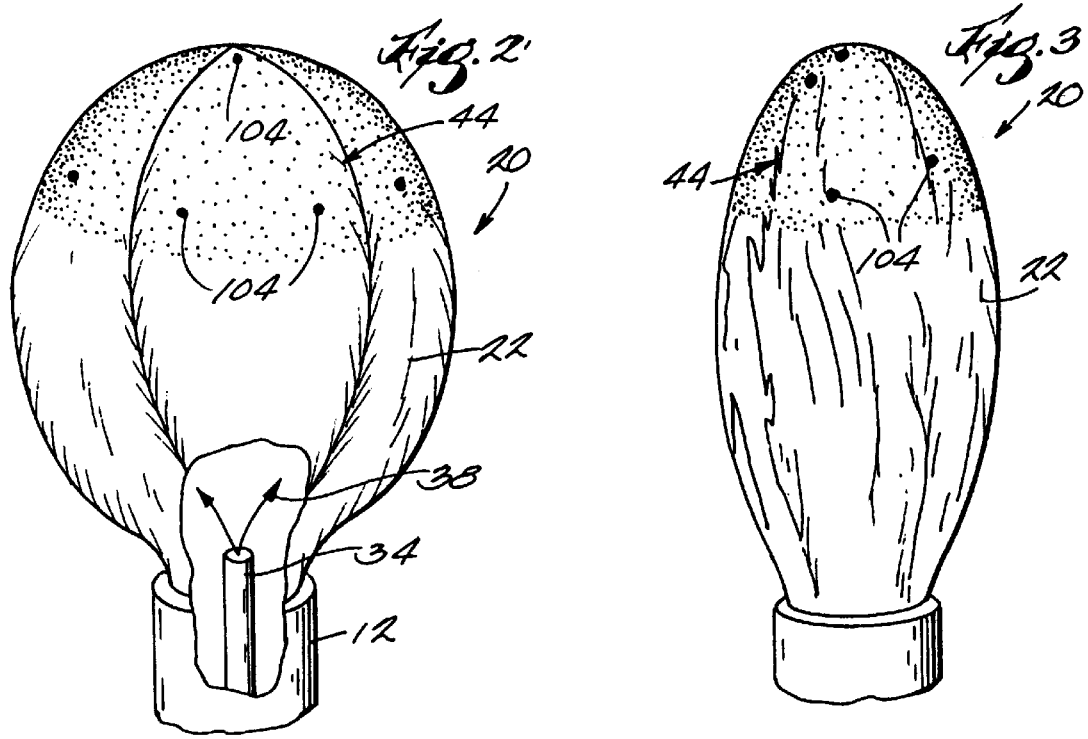
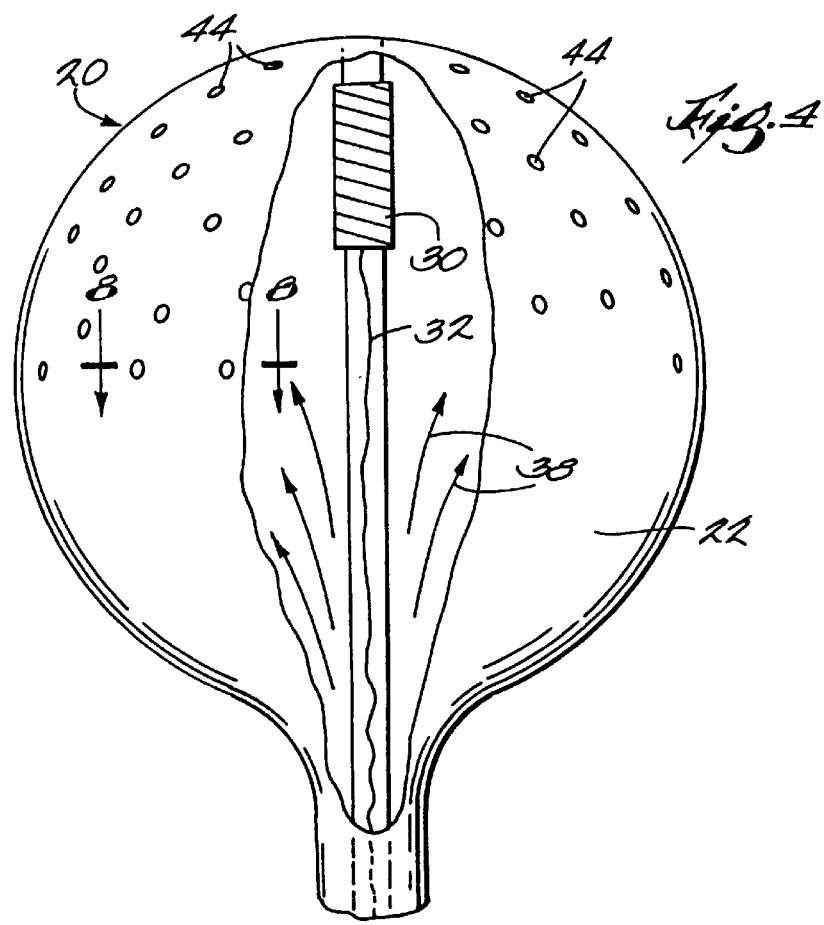

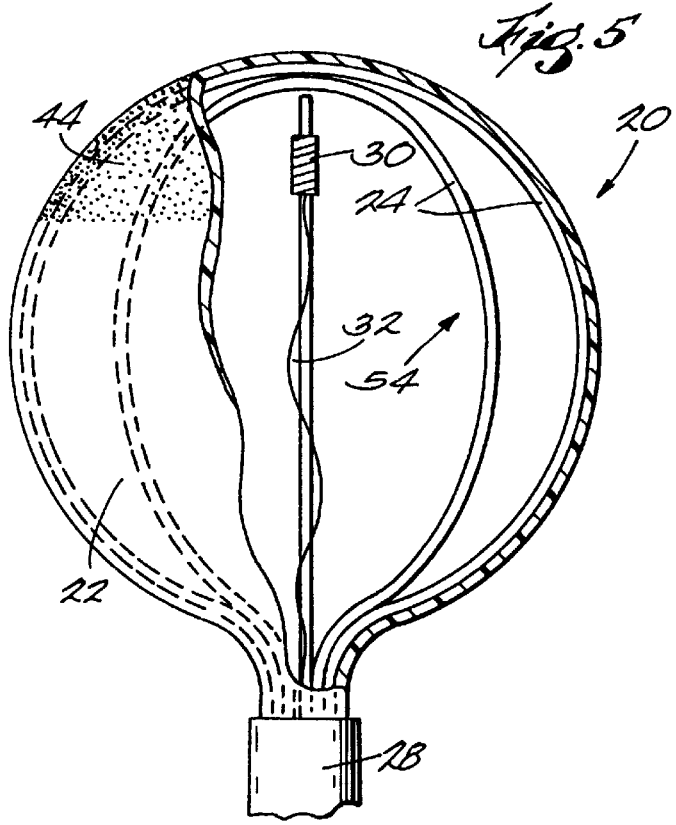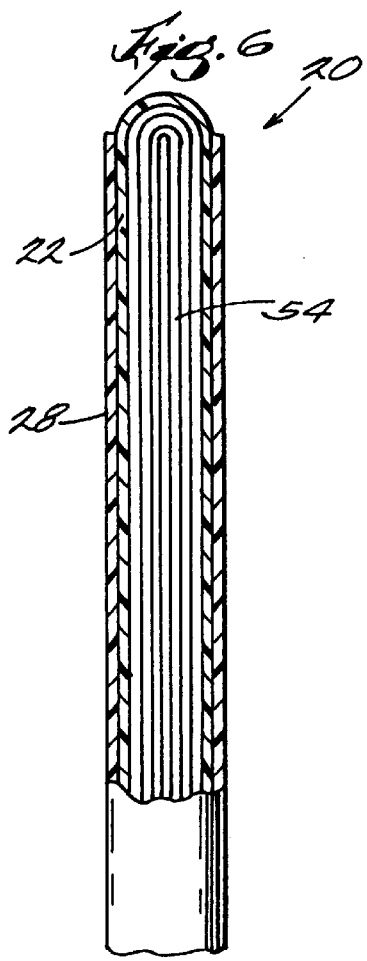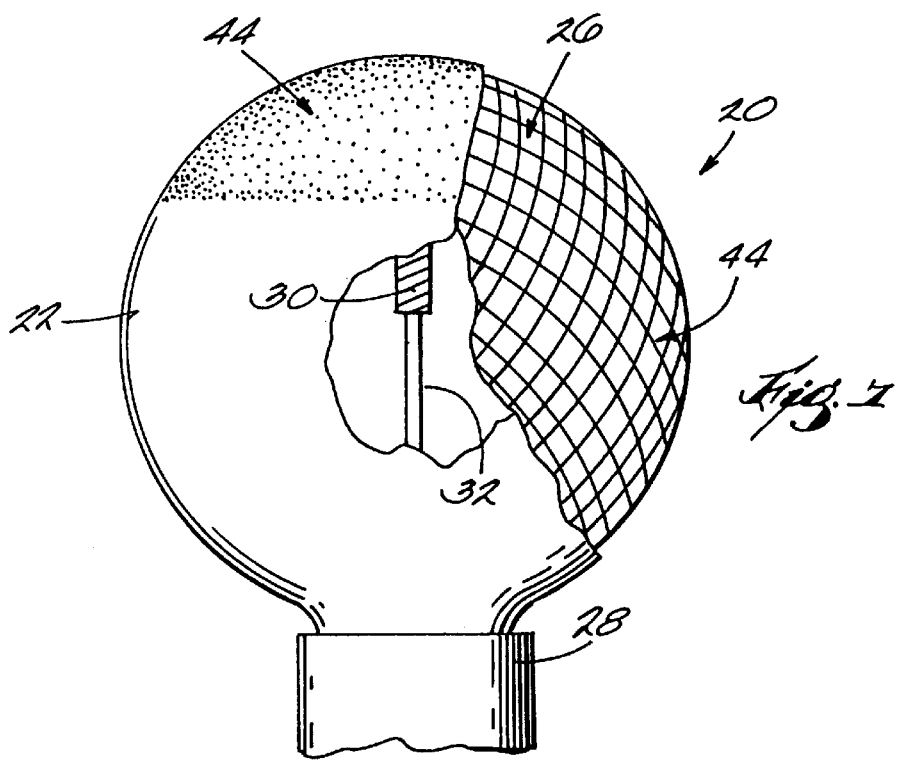

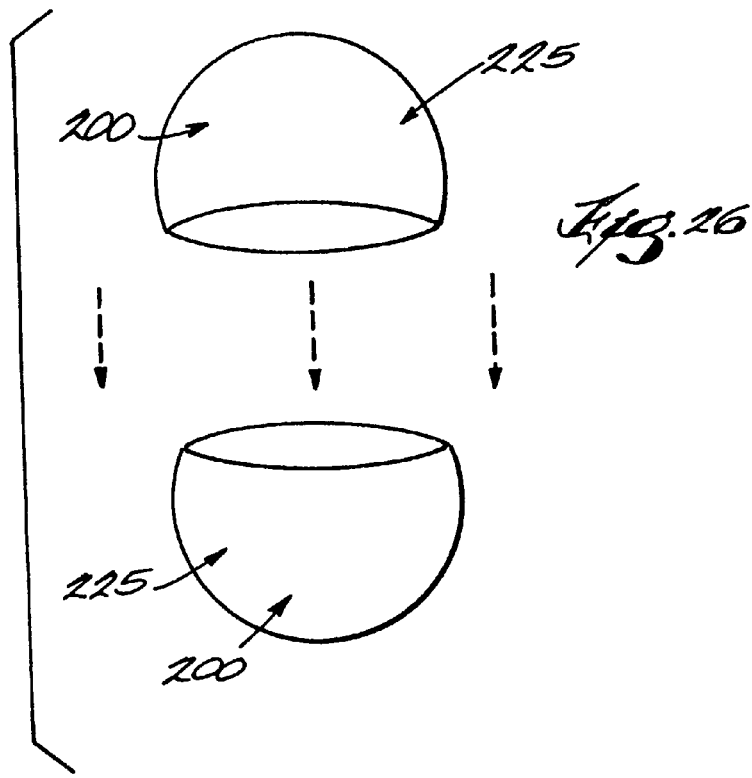
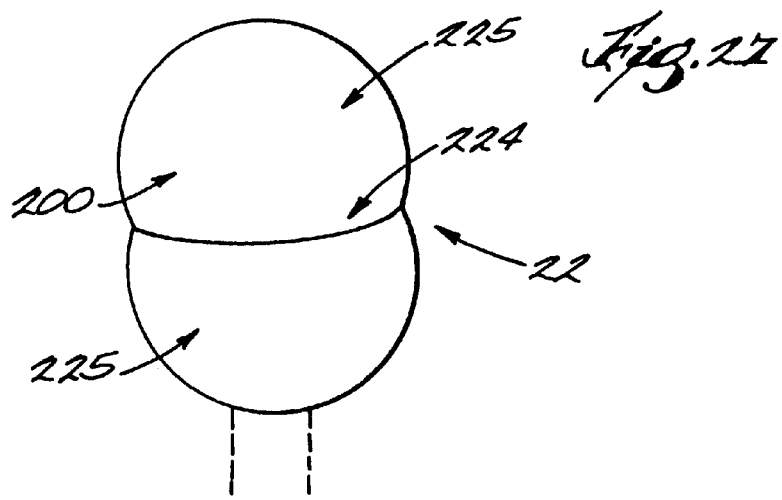

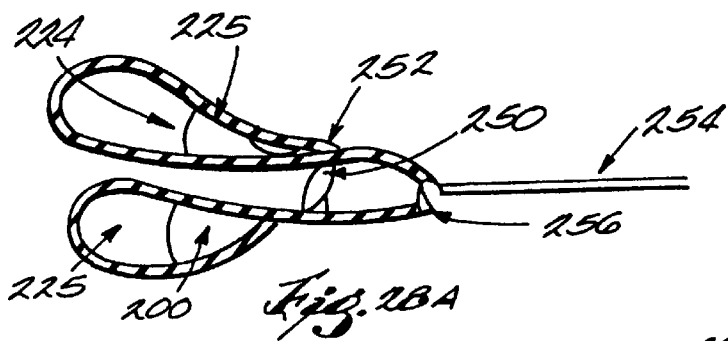
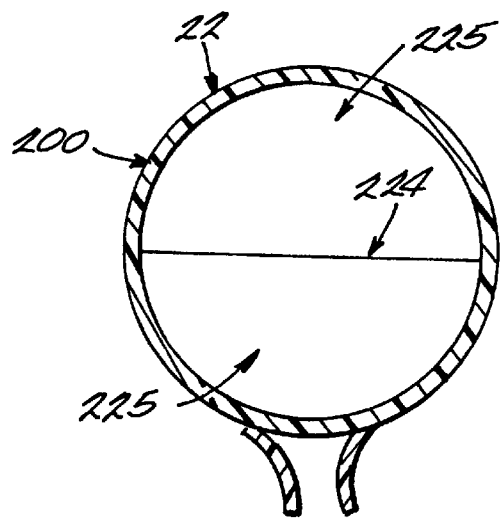
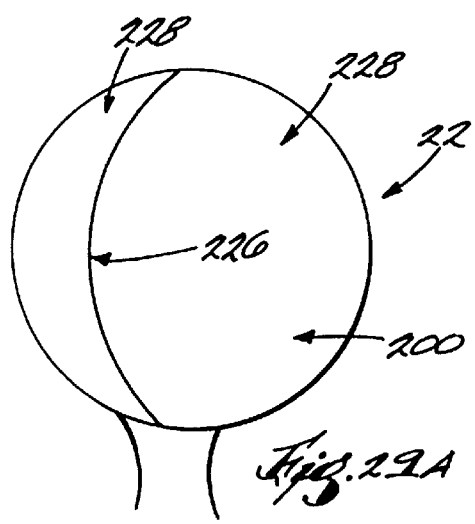
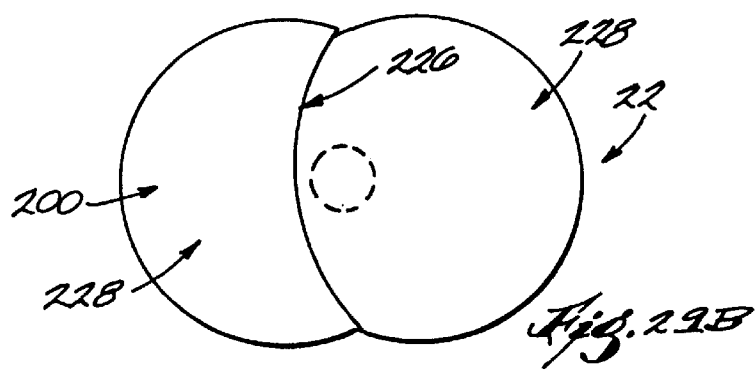

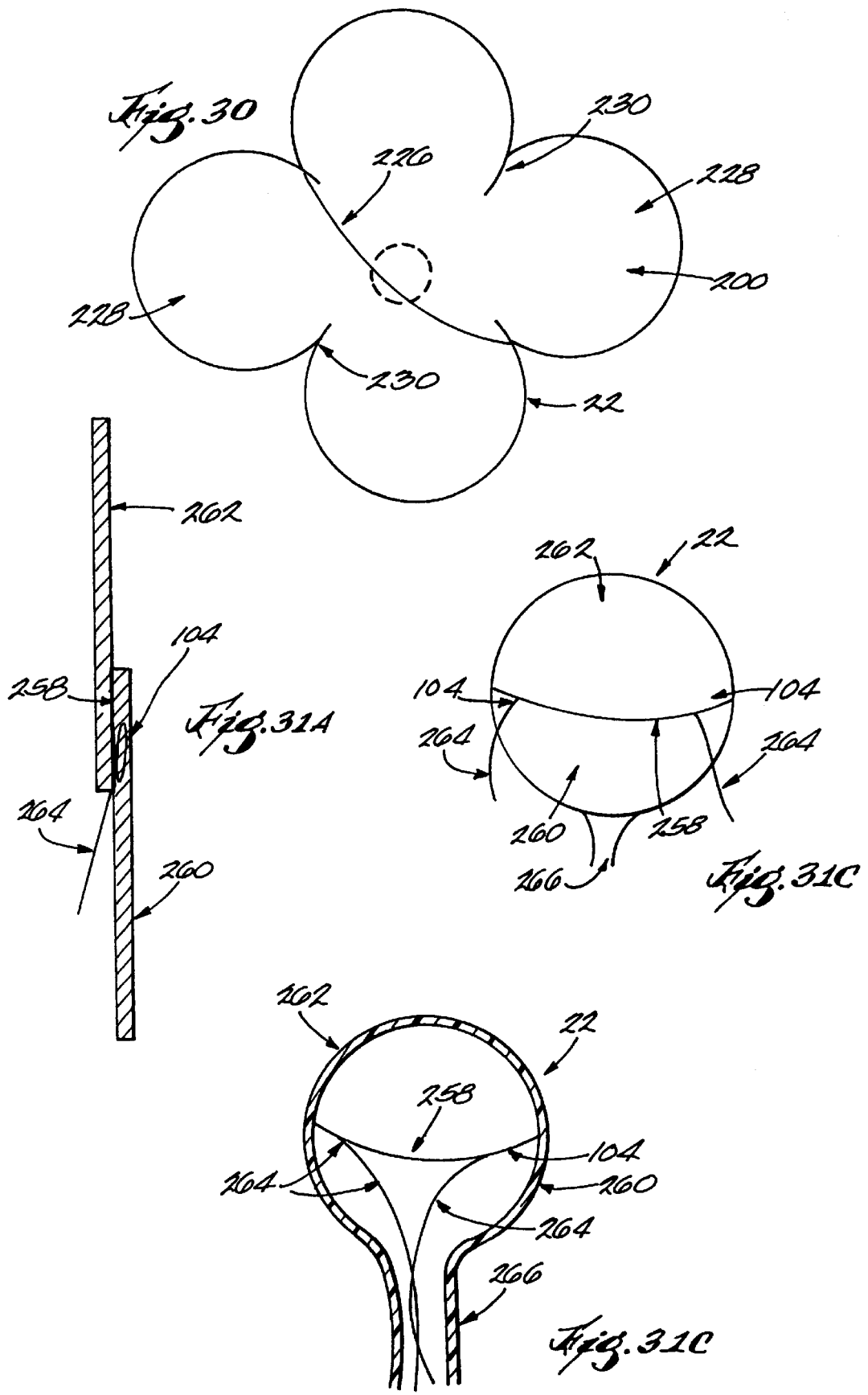

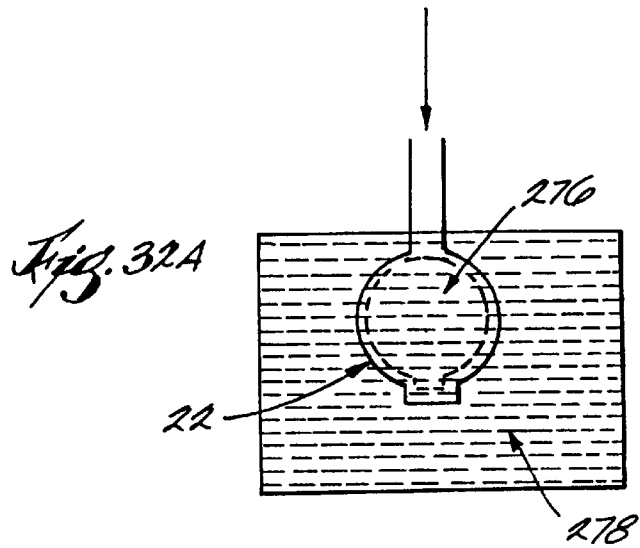
Fig. 32A
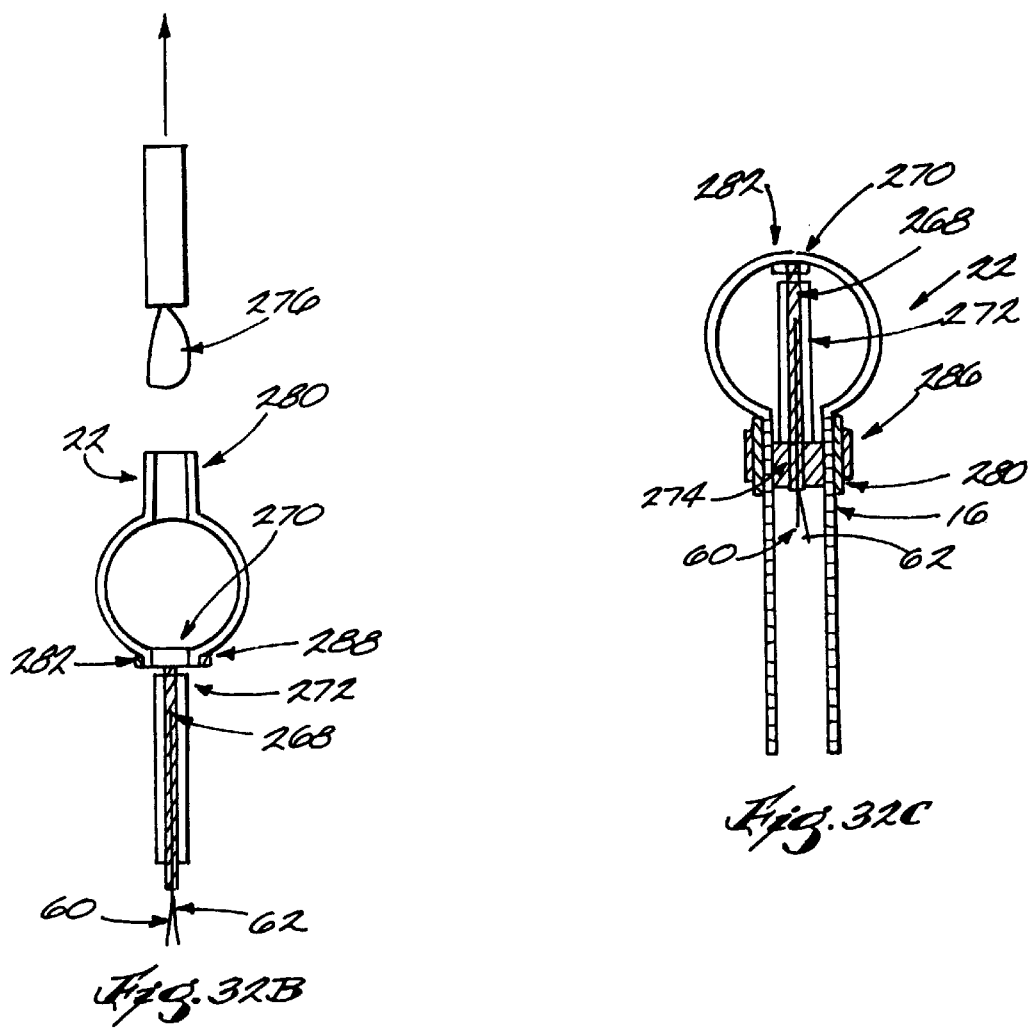
Fig. 32B
Fig. 32C

5,961,513

TISSUE HEATING AND ABLATION SYSTEMS AND METHODS USING POROUS ELECTRODE STRUCTURES

RELATED APPLICATION

This application claims the benefit of U.S. Provisional Applications having Ser. Nos. 60/010,223, 60/010,225 and 60/010,354, all of which were filed on Jan. 19, 1996.

FIELD OF THE INVENTION

The invention generally relates to electrode structures deployed in interior regions of the body. In a more specific sense, the invention relates to electrode structures deployable into the heart for diagnosis and treatment of cardiac conditions.

BACKGROUND OF THE INVENTION

The treatment of cardiac arrhythmias requires electrodes capable of creating tissue lesions having a diversity of different geometries and characteristics, depending upon the particular physiology of the arrhythmia to be treated.

For example, a conventional 8F diameter/4mm long cardiac ablation electrode can transmit radio frequency energy to create lesions in myocardial tissue with a depth of about 0.5 cm and a width of about 10 mm, with a lesion volume of up to 0.2 $cm^3$. These small and shallow lesions are desired in the sinus node for sinus node modifications, or along the A-V groove for various accessory pathway ablations, or along the slow zone of the tricuspid isthmus for atrial flutter (AFL) or AV node slow pathways ablations.

However, the elimination of ventricular tachycardia (VT) substrates is thought to require significantly larger and deeper lesions, with a penetration depth greater than 1.5 cm, a width of more than 2.0 cm, with a lesion volume of at least 1 $cm^3$.

There also remains the need to create lesions having relatively large surface areas with shallow depths.

One proposed solution to the creation of diverse lesion characteristics is to use different forms of ablation energy. However, technologies surrounding microwave, laser, ultrasound, and chemical ablation are largely unproven for this purpose.

The use of active cooling in association with the transmission of DC or radio frequency ablation energy is known to force the electrode-tissue interface to lower temperature values, As a result, the hottest tissue temperature region is shifted deeper into the tissue, which, in turn, shifts the boundary of the tissue rendered nonviable by ablation deeper into the tissue. An electrode that is actively cooled can be used to transmit more ablation energy into the tissue, compared to the same electrode that is not actively cooled. However, control of active cooling is required to keep maximum tissue temperatures safely below about 100° C., at which tissue desiccation or tissue boiling is known to occur.

Another proposed solution to the creation of larger lesions, either in surface area and/or depth, is the use of substantially larger electrodes than those commercially available. Yet, larger electrodes themselves pose problems of size and maneuverability, which weigh against a safe and easy introduction of large electrodes through a vein or artery into the heart.

A need exists for multi-purpose cardiac ablation electrodes that can selectively create lesions of different geometries and characteristics. Multi-purpose electrodes would possess the requisite flexibility and maneuverability permitting safe and easy introduction into the heart. Once deployed inside the heart, these electrodes would possess the capability to emit energy sufficient to create, in a controlled fashion, either large and deep lesions, or small and shallow lesions, or large and shallow lesions, depending upon the therapy required.

SUMMARY OF THE INVENTION

The invention provides various porous electrode assemblies for tissue heating and ablation systems and methods, which enable ionic transport of electrical energy to occur substantially free of liquid perfusion.

The porous electrode assembly that embodies features of the invention includes a wall having an exterior peripherally surrounding an interior area. A lumen conveys a medium containing ions into the interior area. An element couples the medium within the interior area to a source of electrical energy.

According to one aspect of the invention, at least a portion of the wall comprises a porous material sized block passage of macromolecules while allowing passage of ions contained in the medium. The wall thereby enables ionic transport of electrical energy through the porous material to the exterior of the wall.

According to another aspect of the invention, at least a portion of the wall comprises a porous material sized to pass ions contained in the medium without substantial liquid perfusion through the porous material. The wall thereby enables ionic transport of electrical energy through the porous material to the exterior of the wall, without substantial perfusion of liquid through the wall.

According to another aspect of the invention, at least a portion of the wall comprises a porous material sized to pass ions contained in the medium to thereby enable ionic transport of electrical energy through the porous material to the exterior of the wall. According to this aspect of the invention, the porous material has a bubble point value greater than the internal pressure.

According to another aspect of the invention, at least a portion of the wall comprises a hydrophilic porous material sized to pass ions contained in the medium to thereby enable ionic transport of electrical energy through the porous material to the exterior of the wall. According to this aspect of the invention, the porous material has a bubble point value greater than the internal pressure, whereby ionic transport occurs substantially free of liquid perfusion through the porous material.

Other features and advantages of the inventions are set forth in the following Description and Drawings.

BRIEF DESCRIPTION OF THE DRAWINGS

FIG. 1 is a plan view of a system for ablating heart tissue, which includes an expandable porous electrode structure that embodies the features of the invention;

FIG. 2 is an enlarged side elevation view, with portions broken away, of a porous electrode structure usable in association with the system shown in FIG. 1, with the electrode structure shown in its expanded geometry;

FIG. 3 is an enlarged side elevation view of the porous electrode structure shown in FIG. 2, with the electrode structure shown in its collapsed geometry;

FIG. 4 is a further enlarged, somewhat diagrammatic side view, with portions broken away, of the porous electrode structure shown in FIG. 2;

FIG. 5 is an enlarged side elevation view, with portions broken away, of a porous electrode structure usable in association with the system shown in FIG. 1, with the electrode structure shown in its expanded geometry due to the presence of an interior spline support structure;

FIG. 6 is an enlarged side section view of the porous electrode structure shown in FIG. 5, with the electrode structure shown in its collapsed geometry due to the manipulation of an exterior sliding sheath;

FIG. 7 is an enlarged side elevation view, with portions broken away, of a porous electrode structure usable in association with the system shown in FIG. 1, with the electrode structure shown in its expanded geometry due to the presence of an interior interwoven mesh support structure;

FIG. 26 is a somewhat diagrammatic view of two preformed hemispherical body sections of porous electrode body before being joined together into a composite porous electrode body;

FIG. 27 is a side elevation view of the composite porous electrode body formed by joining the two hemispherical sections shown in FIG. 26 together along a circumferential seam;

FIG. 28A is a side section view showing the eversion of the porous electrode body shown in FIG. 27 to place the circumferential seam on the inside of the body, away from direct tissue contact;

FIG. 28B is a side section view of the porous electrode body shown in FIG. 27 after having been everted to place the circumferential seam on the inside of the body;

FIG. 29A is a side elevation view of a porous electrode body formed by joining two hemispherical sections along an axial seam and after eversion to place the axial seam on the inside of the body;

FIG. 29B is a top view of the porous electrode body with the everted axial seam shown in FIG. 29A;

FIG. 30 is a top view of a porous electrode body formed by joining two hemispherical sections along a main axial seam, with additional intermediate axial seams to segment the body, after eversion to place the axial seams on the inside of the body;

FIG. 31A is an enlarged side sectional view of a seam joining two sheets of porous material together to form an electrode body, with a temperature sensing element encapsulated within the seam, and before eversion of the body;

FIG. 31B is a side elevation view of the seamed body, shown partially in FIG. 31A, with temperature sensing elements encapsulated in the seam, and before eversion of the body;

FIG. 31C is a side section view of the body shown in FIG. 31B after eversion, placing the seam and the signal wires of the temperature sensing elements inside the body;

FIG. 32A is a somewhat diagrammatic view of a porous electrode body being formed from a regenerated cellulose material by dipping using an expandable fixture;

FIG. 32B is the dip-formed body shown being formed in FIG. 32A, after removal of the expandable fixture and attachment of a fixture with steering assembly to the distal end of the body, and before eversion;

FIG. 32C is the dip-formed body with distal fixture and steering assembly, shown in FIG. 32B, after eversion;

Figure 8:
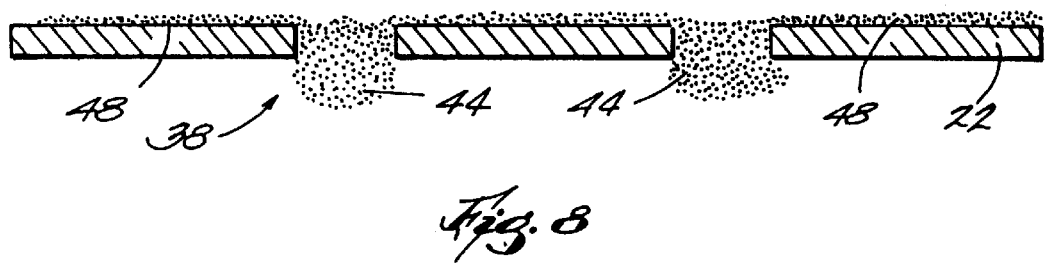
FIG. 8 is an enlarged, somewhat diagrammatic enlarged view, taken generally along line 8—8 of FIG. 4, showing the ionic current densities across the pores of the electrode body shown in FIG. 4.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows a tissue ablation system 10 that embodies the features of the invention.

The system 10 includes a flexible catheter tube 12 with a proximal end 14 and a distal end 16. The proximal end 14 carries a handle 18. The distal end 16 carries an electrode structure 20, which embodies features of the invention. The purpose of the electrode structure 20 is to transmit ablation energy.

As FIGS. 2 and 3 best show, the electrode structure 20 includes an expandable-collapsible body 22. The geometry of the body 22 can be altered between a collapsed geometry (FIG. 3) and an enlarged, or expanded, geometry (FIG. 2). In the illustrated and preferred embodiment, liquid pressure is used to inflate and maintain the expandable-collapsible body 22 in the expanded geometry.

In this arrangement (see FIG. 2), the catheter tube 12 carries an interior lumen 34 along its length. The distal end of the lumen 34 opens into the hollow interior of the expandable-collapsible body 22. The proximal end of the lumen 34 communicates with a port 36 (see FIG. 1) on the handle 18. The liquid inflation medium (arrows 38 in FIG. 2) is conveyed under positive pressure through the port 36 and into the lumen 34. The liquid medium 38 fills the interior of the expandable-collapsible body 22. The liquid medium 38 exerts interior pressure to urge the expandable-collapsible body 22 from its collapsed geometry to the enlarged geometry.

This characteristic allows the expandable-collapsible body 22 to assume a collapsed, low profile (ideally, less than 8 French diameter, i.e., less than about 0.267 cm) when introduced into the vasculature. Once located in the desired position, the expandable-collapsible body 22 can be urged into a significantly expanded geometry of, for example, approximately 7 to 20 mm.

As FIGS. 5 to 7 show, the structure 20 can include, if desired, a normally open, yet collapsible, interior support structure 54 to apply internal force to augment or replace the force of liquid medium pressure to maintain the body 22 in the expanded geometry. The form of the interior support structure 54 can vary. It can, for example, comprise an assemblage of flexible spline elements 24, as shown in FIG. 5, or an interior porous, interwoven mesh or an open porous foam structure 26, as shown in FIG. 7.

In these arrangements (see FIG. 6), the internally supported expandable-collapsible body 22 is brought to a collapsed geometry, after the removal of the inflation medium, by outside compression applied by an outer sheath 28 (see FIG. 6), which slides along the catheter tube 12. As FIG. 6 shows, forward movement of the sheath 28 advances it over the expanded expandable-collapsible body 22. The expandable-collapsible body 22 collapses into its low profile geometry within the sheath 28. Rearward movement of the sheath 28 (see FIGS. 5 or 7) retracts it away from the expandable-collapsible body 22. Free from the confines of the sheath 48, the interior support structure 54 springs open to return the expandable-collapsible body 22 to its expanded geometry to receive the liquid medium.

As FIG. 4 best shows, the structure 20 further includes an interior electrode 30 formed of an electrically conductive material carried within the interior of the body 22. The material of the interior electrode 30 has both a relatively high electrical conductivity and a relatively high thermal conductivity. Materials possessing these characteristics include gold, platinum, platinum/iridium, among others. Noble metals are preferred.

An insulated signal wire 32 is coupled to the electrode 30. The signal wire 32 extends from the electrode 30, through the catheter tube 12, to an external connector 38 on the handle 18 (see FIG. 1). The connector 38 electrically couples the electrode 30 to a radio frequency generator 40.

In the preferred and illustrated embodiment (see FIG. 1), a controller 42 is associated with the generator 40, either as an integrated unit or as a separate interface box. The controller 42 governs the delivery of radio frequency ablation energy to the electrode 30 according to preestablished criteria. Further details of this aspect of the system 10 will be described later.

According to the invention, the liquid medium 38 used to fill the body 22 includes an electrically conductive liquid. The liquid 38 establishes an electrically conductive path, which conveys radio frequency energy from the electrode 30. In conjunction, the body 22 comprises an electrically non-conductive thermoplastic or elastomeric material that contains pores 44 on at least a portion of its surface. The pores 44 of the porous body 22 (shown diagrammatically in enlarged form in FIG. 4 for the purpose of illustration) establishes ionic transport of ablation energy from the electrode 30, through the electrically conductive medium 38, to tissue outside the body.

Preferably, the liquid 38 possesses a low resistivity to decrease ohmic loses, and thus ohmic heating effects, within the body 22. In the illustrated and preferred embodiment, the liquid 38 also serves the additional function as the inflation medium for the body, at least in part.

The composition of the electrically conductive liquid 38 can vary. In the illustrated and preferred embodiment, the liquid 38 comprises a hypertonic saline solution, having a sodium chloride concentration at or near saturation, which is about 9% weight by volume. Hypertonic saline solution has a low resistivity of only about 5 ohm·cm, compared to blood resistivity of about 150 ohm·cm and myocardial tissue resistivity of about 500 ohm·cm.

Alternatively, the composition of the electrically conductive liquid medium 38 can comprise a hypertonic potassium chloride solution. This medium, while promoting the desired ionic transfer, requires closer monitoring of rate at which ionic transport occurs through the pores 44, to prevent potassium overload. When hypertonic potassium chloride solution is used, it is preferred keep the ionic transport rate below about 10 mEq/min.

The system 10 as just described is ideally suited for ablating myocardial tissue within the heart. In this environment, a physician moves the catheter tube 12 through a main vein or artery into a heart chamber, while the expandable-collapsible body 22 of the electrode structure 20 is in its low profile geometry. Once inside the desired heart chamber, the expandable-collapsible body 22 is enlarged into its expanded geometry and the region containing pores 44 is placed into contact with the targeted region of endocardial tissue.

Due largely to mass concentration differentials across the pores 44, ions in the medium 38 will pass into the pores 44, because of concentration differential-driven diffusion. Ion diffusion through the pores 44 will continue as long as a concentration gradient is maintained across the body 22. The ions contained in the pores 44 provide the means to conduct current across the body 22.

Radio frequency energy is conveyed from the generator 40 to the electrode 30, as governed by the controller 42. When radio frequency (RF) voltage is applied to the electrode 30, electric current is carried by the ions within the pores 44. The RF currents provided by the ions result in no net diffusion of ions, as would occur if a DC voltage were applied, although the ions do move slightly back and forth during the RF frequency application. This ionic movement (and current flow) in response to the applied RF field does not require perfusion of liquid in the medium 38 through the pores 44.

The ions convey radio frequency energy through the pores 44 into tissue to a return electrode, which is typically an external patch electrode (forming a unipolar arrangement). Alternatively, the transmitted energy can pass through tissue to an adjacent electrode in the heart chamber (forming a bipolar arrangement). The radio frequency energy heats the tissue, mostly ohmically, forming a lesion.

The electrical resistivity of the body 22 has a significant influence on the lesion geometry and controllability. It has been discovered that ablation with devices that have a low-resistivity body 22 requires more RF power and results in deeper lesions. On the other hand, devices that have a high-resistivity body 22 generate more uniform heating, therefore, improve the controllability of the lesion. Because of the additional heat generated by the increased body resistivity, less RF power is required to reach similar tissue temperatures after the same interval of time. Consequently, lesions generated with high-resistivity bodies 22 usually have smaller depth.

Generally speaking, lower resistivities values for the body 22 below about 500 ohm·cm result in deeper lesion geometries. Likewise, higher resistivities for the body 22 at or above about 500 ohm·cm result in more shallow lesion geometries.

The electrical resistivity of the body 22 can be controlled by specifying the pore size of the material, the porosity of the material, and the water adsorption characteristics (hydrophilic versus hydrophobic) of the material.

SPECIFYING PORE SIZE

The size of the pores 44 in the body 22 can vary. Pore diameters smaller than about 0.1 $\mu$m, typically used for blood oxygenation, dialysis, or ultrafiltration, can be used for ionic transfer according to the invention. These small pores, which can be visualized by high-energy electron microscopes, retain macromolecules, but allow ionic transfer through the pores in response to the applied RF field, as above described. With smaller pore diameters, pressure driven liquid perfusion through the pores 44 is less likely to accompany the ionic transport, unless relatively high pressure conditions develop within the body 22.

Larger pore diameters, typically used for blood microfiltration, can also be used for ionic transfer according to the invention. These larger pores, which can be seen by light microscopy, retain blood cells, but permit passage of ions in response to the applied RF field. Generally speaking, pore sizes below 8 $\mu$m will block most blood cells from crossing the membrane. With larger pore diameters, pressure driven liquid perfusion, and the attendant transport of macromolecules through the pores 44, is also more likely to occur at normal inflation pressures for the body 22.

Still larger pore sizes can be used, capable of accommodating formed blood cell elements. However, considerations of overall porosity, perfusion rates, and lodgment of blood cells within the pores of the body 22 must be taken more into account as pore size increase.

Conventional porous, biocompatible membrane materials used for blood oxygenation, dialysis, blood filtration such as plasmapheresis can serve as the porous body 22. Such membrane materials can be made from, for example, regenerated cellulose, nylon, polycarbonate, polyvinylidene fluoride (PTFE), polyethersulfone, modified acrylic copolymers, and cellulose acetate.

Alternatively, porous or microporous materials may be fabricated by weaving a material (such as nylon, polyester, polyethylene, polypropylene, fluorocarbon, fine diameter stainless steel, or other fiber) into a mesh having the desired pore size and porosity. The use of woven materials is advantageous, because woven materials are very flexible as small diameter fibers can be used to weave the mesh. By using woven materials, uniformity and consistency in pore size also can be achieved.

Spectrum Medical Industries, Inc. (Houston, Texas) commercially supplies nylon and polyester woven materials with pore sizes as small as 5 $\mu$m with porosities of 2%. Stainless steel woven materials with pore sizes as small as 30 $\mu$m with porosities of 30% can also be obtained from Spectrum Medical Industries, Inc. Manufacturers, such as Tetko, also produce woven materials meeting the desired specifications. Woven materials with smaller pore sizes may be achieved depending on the material.

Woven meshes may be fabricated by conventional techniques, including square mesh or twill mesh. Square mesh is formed by conventional "over and under" methods. Twill mesh is formed by sending two fibers over and under. The materials may be woven into a 3-dimensional structure, such as a tube or a sphere. Alternatively, the materials may be woven into a flat, 2-dimensional sheet and formed (heat forming, thermal bonding, mechanical deformation, ultrasonic welding etc.) into the desired 3-dimensional geometry of the body 22.

Pore size can be specified using bubble point measurements. The bubble point value is defined as the pressure required to force liquid through the membrane, which is a function mainly of pore size (given the same water adsorption characteristic). The standard for measuring bubble point value is ASTM F316-80.

Pore size correlates with the expected liquid flow resistance of the membrane. As a general proposition, larger pores allow more liquid to flow through the pores and at higher flow rates. Likewise, smaller pores limit the volume and rate of liquid perfusion through the pores. At a point, a pore will be small enough to effectively block liquid perfusion, except at very high pressure, while nevertheless enabling ionic transport to occur in the manner described above.

Low or essentially no liquid perfusion through the pores 44 is preferred. Limited or essentially no liquid perfusion through the pores 44 is beneficial for several reasons. First, it limits salt or water overloading, caused by transport of the hypertonic solution into the blood pool. This is especially true, should the hypertonic solution include potassium chloride, as observed above.

Furthermore, limited or essentially no liquid perfusion through the pores 44 allows ionic transport to occur without disruption. When undisturbed by attendant liquid perfusion, ionic transport creates a continuous virtual electrode 48 (see FIG. 8) at the body 22-tissue interface. The virtual electrode 48 efficiently transfers RF energy without need for an electrically conductive metal surface.

The bubble point value in psi for a given porous material also aids in specifying the nature of ionic transport the porous material supports, thereby indicating its suitability for tissue ablation.

When the bubble point value for a given porous material exceeds the pressure required to inflate the body 22 (i.e., inflation pressure), it is possible to pressure inflate the body 22 into its expanded geometry, without promoting pressure-driven liquid perfusion through the pores 44 of the material. Specifying a material with a bubble point value greater than body inflation pressure assures that ionic transfer through the pores 44 occurs without attendant liquid perfusion through the pores 44.

A bubble point value that is significantly less than the body inflation pressure also indicates that the body 22 containing the porous material may never reach its intended expanded geometry, because of excessive liquid perfusion through the pores 44.

On the other hand, the bubble point value of the porous material should not exceed the tensile strength of the porous material. By specifying this relationship between bubble point value and tensile strength, liquid perfusion will occur before abnormally high pressures develop, lessening the chance that the body 22 will rupture.

The bubble point value specification mediates against the use of larger pore size materials. Larger pore size materials pose problems of inflation and excessive fluid perfusion through the membrane.

SPECIFYING POROSITY

The placement of the pores 44 and the size of the pores 44 determine the porosity of the body 22. The porosity represents the space on the body 22 that does not contain material, or is empty, or is composed of pores 44. Expressed as a percentage, porosity represents the percent volume of the body 22 that is not occupied by the body material.

For materials having a porosity greater than about 10%, porosity P (in %) can be determined as follows:

$$P = 100\left(1 - \frac{\rho_b}{\rho_m}\right)$$

where:
$\rho_b$ is the density of the body 22 as determined by its weight and volume, and
$\rho_m$ is the density of the material from which the body 22 is made.

To derive porosity for materials having a porosity of less than about 10%, a scanning electron microscope can be used to obtain the number of pores and their average diameter. Porosity P (in %) is then derived as follows:

$$P = N\pi\left(\frac{d^2}{4}\right)$$

where:
N is the pore density and equals $(p_n/a)$,
$P_n$ is the number of pores in the body 22,
a is the total porous area of the body 22 (in cm$^2$), and
$\pi$ is the constant 3.1416...,
d is the average diameter of the pores (in cm).

The magnitude of the porosity affects the liquid flow resistance of the body 22, as discussed above. The equivalent electrical resistivity of the body 22 also depends on its porosity. Low-porosity materials have high electrical resistivity, whereas high-porosity materials have low electrical resistivity. For example, a material with 3% porosity, when exposed to 9% hypertonic solution (resistivity of 5 ohm·cm), may have an electrical resistivity comparable to that of blood or tissue (between 150 and 450 ohm·cm).

The distribution of pores 44 for a given porosity also affects the efficiency of ionic transport. Given a porosity value, an array of numerous smaller pores 44 is preferred, instead of an array of fewer but larger pores. The presence of numerous small pores 44 distributes current density so that the current density at each pore 44 is less. With current density lessened, the ionic flow of electrical energy to tissue occurs with minimal diminution due to resistive heat loss.

An array of numerous smaller pores 44 is also preferred, instead of an array of fewer but larger pores, because it further helps to impose favorably large liquid flow resistance. The presence of numerous small pores 44 limits the rate at which liquid perfusion occurs through each pore 44.

A dynamic change in resistance across a body 22 can be brought about by changing the diameter of the body 22 made from a porous elastic material, such as silicone. In this arrangement, the elastic body 22 is made porous by drilling pores of the same size in the elastic material when in a relaxed state, creating a given porosity. As the elastic body 22 is inflated, its porosity remains essentially constant, but the wall thickness of the body 22 will decrease. Thus, with increasing diameter of the body 22, the resistance across the body 22 decreases, due to decreasing wall thickness and increasing surface area of the body 22. As the surface area of the body 22 increases by a factor of two, the thickness of the body 22 will decrease by a factor of two, resulting in a decrease in resistance by a factor of four.

As a result, the desired lesion geometry may be specified according to the geometry of the body 22. This enables use of the same porous body 22 to form small lesions, shallow and wide lesions, or wide and deep lesions, by controlling the geometry of the body 22.

Preferably, the porous body 22 should possess consistent pore size and porosity throughout the desired ablation region. Without consistent pore size and porosity, difference in electrical resistance of the body 22 throughout the ablation region can cause localized regions of higher current density and, as a result, higher temperature. If the difference in electrical resistance is high enough, the lesion may not be therapeutic, because it may not extend to the desired depth or length. Furthermore, nonuniform areas of low porosity in the body 22 can themselves experience physical damage as a result of the localized heating effects.

SPECIFYING WATER ADSORPTION CHARACTERISTICS

The porous material for the body 22 may be either hydrophobic or hydrophilic. However, the water adsorption characteristics of the porous material also affect the electrical resistivity of the material.

For materials of the same pore size and porosity, materials that are hydrophilic possess greater capacity to provide ionic transfer of radiofrequency energy without significant liquid flow through the material. Ions suspended in the medium are more likely to fully occupy the pores of a hydrophilic material in the absence of a driving pressure exceeding the bubble point value of the material, compared to hydrophobic materials. The presence of these ions within the pores in the hydrophilic materials provides the capacity of ionic current flow with no need for liquid perfusion through the pores. As a result, pore sizes may be decreased more readily with hydrophilic materials, thereby raising the bubble point value to minimize liquid perfusion, without adversely affecting desired ionic current-carrying capacities. Furthermore, the relationship between porosity and resistivity is more direct in the case of hydrophilic materials than with hydrophobic materials.

Some forms of nylon (e. g., nylon 6 or nylon 6/6) are examples of hydrophilic materials having high water adsorption suitable for use as a porous electrode. The nylon sample identified in Example 3 below has 4.0% to 4.2% moisture adsorption at 65% relative humidity and a temperature of 20° C.

Nevertheless, conventional medical grade "balloon" materials, such as PET and PeBax, are hydrophobic. Ions in the medium are less likely to occupy the pore of a hydrophobic membrane, absent a driving pressure exceeding the bubble point value of the material, compared to a hydrophilic material. As a result, hydrophobic materials are more likely to require liquid flow through the pores to carry ions into the pores, to thereby enable transmission of electrical energy across the porous material. With such materials, the inflation pressure of the body should exceed the bubble point value to enable effective ionic transport.

Furthermore, due to the higher surface tension of hydrophobic material, which tends to restrict ion flow into the pores, hydrophobic materials also exhibit a greater tendency to cause material breakdown at the pores, compared with hydrophilic materials. The large potential differences across each pore in a hydrophobic material may cause dissociation of water molecules, dielectric breakdown of the membrane material, and localized overheating. The breakdown is associated with high temperature effects and, depending on the material, can open up the pores, burn the material surrounding the pores, and generally degrade the material. In addition, material breakdown can produce hazardous tissue effects similar to DC ablation, such as tissue charring.

Therefore, changing the water adsorption characteristics of a porous material from more hydrophobic to more hydrophilic can offset undesired electrical characteristics, without changing pore size or porosity. For example, the incidence of material breakdown due to high current densities and potential drops at the pores can be reduced by increasing the porosity of the material. However, the incidence of material breakdown can be reduced or eliminated without altering the porosity, by selecting a material that is hydrophilic; for example, materials such as regenerated cellulose, nylon 6, and nylon 6/6, which typically have high water adsorption. Alternatively, coatings or surface treatments may be applied to a less hydrophilic material making it more hydrophilic. For example, some materials can be dipped into a specially formulated hydrophilic coating and exposed to ultraviolet light to bind the coating to the material surface. This approach is especially advantageous when conventional "balloon" materials are used for the body 22, provided the coating withstands ablation temperatures without degrading.

Other measures can be employed to offset other undesired electrical characteristics due to pore size or porosity or water adsorption properties. For example, for larger pore materials, or when porous hydrophilic materials are used, the perfusion rate can be controlled by controlling fluid pressures across the body 22.

Alternatively, for larger pore materials, or when porous hydrophilic materials are used, a material can be added to the hypertonic solution to increase its viscosity, thereby decreasing its perfusion rate. Examples of materials that can be added to increase viscosity include ionic contrast (radiopaque) substances or nonionic glycerol or concentrated mannitol solutions.

For example, the electrical performance of woven materials having larger pore sizes may be aided by the addition of an ionic radiopaque contrast material like Renografin®-76. By adding a radiopaque material to the aqueous solution, the body 22 may be seen under fluoroscopy (or echocardiography, depending on the contrast material). The flow resistance of the porous material will effectively increase, due to the increased viscosity of the medium.

The use of ionic materials to increase viscosity need not excessively increase the resistivity of the membrane, depending on the concentration of the ionic material. The following Table 1 summarizes the results of in vitro experiments, using an ionic radiopaque material with a woven nylon 13.0 mm disk probe.

TABLE 1

Effects of Ion Contrast Material on Ablation with a Woven Nylon Disk

| Fluid Medium | Set Temperature | Average Power | Average Impedance | Lesion Depth | Lesion Length |
|---|---|---|---|---|---|
| 9% NaCl | 90° C. | 23 W | 68 Ω | 9.9 mm | 21.0 mm |
| 50%–9% NaCl | 90° C. | 13 W | 85 Ω | 8.4 mm | 16.6 mm |
| 50%-Contrast Contrast Material | 90° C. | 14 W | 120 Ω | 8.6 mm | 17.9 mm |

NOTE: All lesion dimensions are based on the 60° C. discoloration characteristic.

Table 1 shows that the ionic contrast medium can reduce the power required to achieve equivalent ablation results and still create desired lesions.

Figure 9:
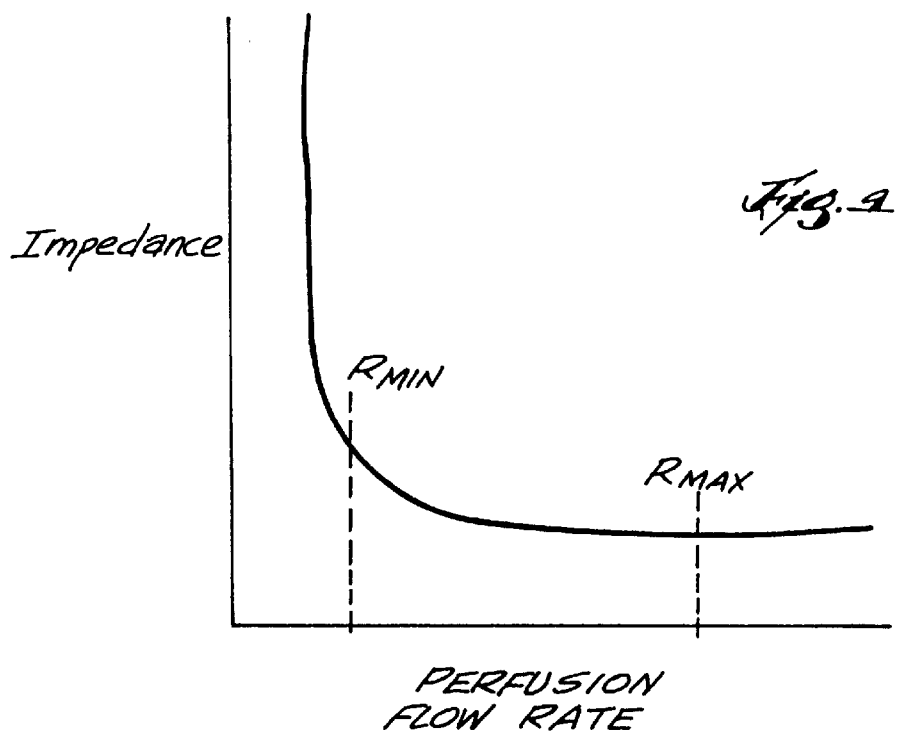
FIG. 9 is a graph showing the relationship between sensed impedance and ionic transport through the pores of the electrode body shown in FIG. 4.

For porous materials, either hydrophilic or hydrophobic, the system 10 can include a device to sense impedance proximate to the body-tissue interface. As FIG. 9 shows, impedance decreases with increasing liquid perfusion flow rate, until a limit point is reached, at which impedance stabilizes despite increasing perfusion rates. By sensing impedance, it is possible to control perfusate flow between a minimum flow rate $R_{MIN}$ (at which impedance is too high) and a maximum flow rate $R_{MAX}$ (above which potential salt or water overload conditions come into existence).

The surface area of the electrode 30 bathed in the electrically conductive medium within the body can be increased to enhance ionic transfer. However, the desired characteristics of small geometry collaspsibility and overall flexibility of the body impose practical constraints upon electrode size.

The proximity of the electrode 30 to the pores 44 of the body 22 also enhances the efficiency of ionic transfer through the electrically conductive medium. Again, the structural characteristics of presenting a flexible, small collapsed profile create practical constraints upon this consideration.

Forming the Body 22

The expandable-collapsible body 22 can be formed about the exterior or interior of a glass mold. In this arrangement, the external dimensions of the mold match the desired expanded geometry of the expandable-collapsible body 22. The mold is dipped in a desired sequence into a solution of the body material until the desired wall thickness is achieved. The mold is then etched away, leaving the formed expandable-collapsible body 22.

Alternatively, the expandable-collapsible body 22 may also be blow molded from extruded tubing. In this arrangement, the body 22 is sealed at one end using adhesive or thermal fusion. The opposite end of the body 22 is left open. The sealed expandable-collapsible body 22 is placed inside the mold. An inflation medium, such as high pressure gas or liquid, is introduced through the open tube end. The mold is exposed to heat as the tube body 22 is inflated to assume the mold geometry. The formed expandable-collapsible body 22 is then pulled from the mold.

The porosity of the body 22 can be imparted either before or after molding by $CO_2$ laser, eximer laser, YAG laser, high power YAG laser, electronic particle bombardment, and the like.

As earlier discussed, coatings or surface treatments may also be applied to make the surface more hydrophilic to improve the electrical properties of the body 22 for tissue ablation.

Commercially available porous materials can also be formed into the body 22. For those materials having poor bonding properties that are formed by chemical processes, such as the regenerated cellulose, the material may be chemically formed into a three-dimensional geometry by a dipping process (as generally shown in FIG. 32A and as will be described later), injection molding, or by varying the diameter and geometry during extrusion.

For those materials that can be thermally bonded, laser welded, ultrasonically welded, and adhesively bonded, there are various ways that make use of these bonding or welding techniques to form a three-dimensional geometry from a sheet of the material may be employed. Fixtures and mandrels can be used to form the body 22 in conjunction with heat and pressure.

Figure 19:
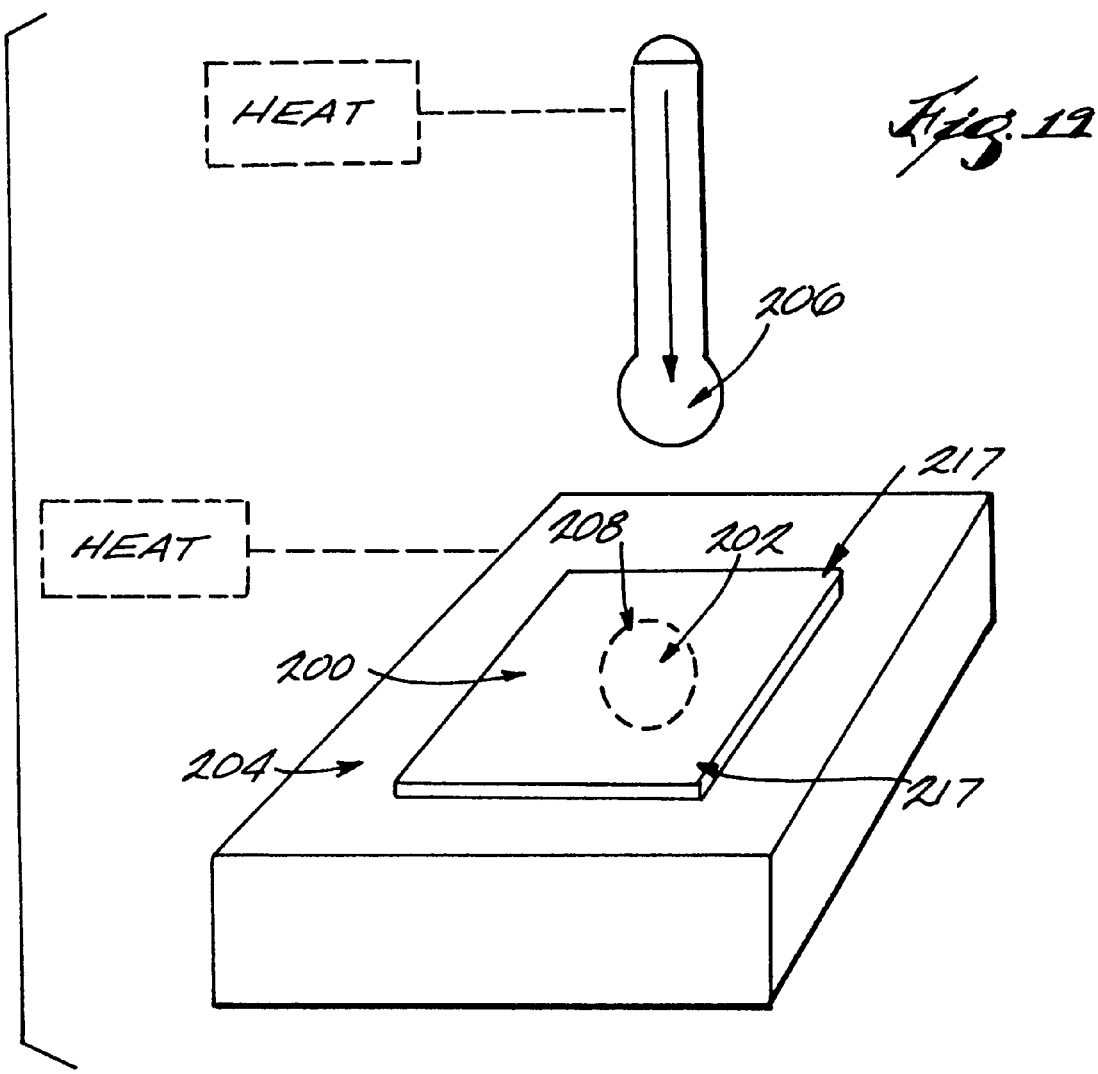
FIG. 19 is a somewhat diagrammatic view of a fixture and mandrel for forming a hemispherical geometry for the distal end of a porous electrode body from a flat sheet of porous material.

FIGS. 19 to 23 show a preferred way for forming a sheet of porous material 200 into the desired three dimensional geometry of an ablation body 22. As FIG. 19 shows, the sheet 200 is placed over a forming cavity 202 on a fixture 204. The geometry of the forming cavity 202 corresponds to the geometry desired for the distal end of the body 22. In the illustrated embodiment, the geometry is generally hemispherical.

Figure 20:
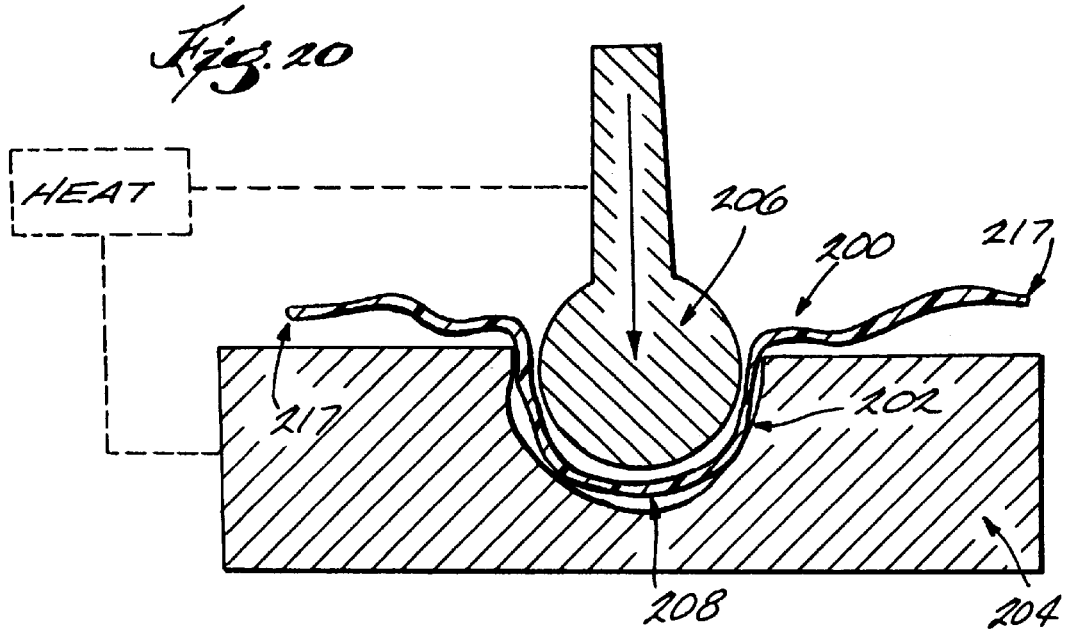
FIG. 20 is a side sectional view of the fixture and mandrel shown in FIG. 19 in the process of forming the hemispherical distal end geometry in a flat sheet of porous material.
Figure 21:
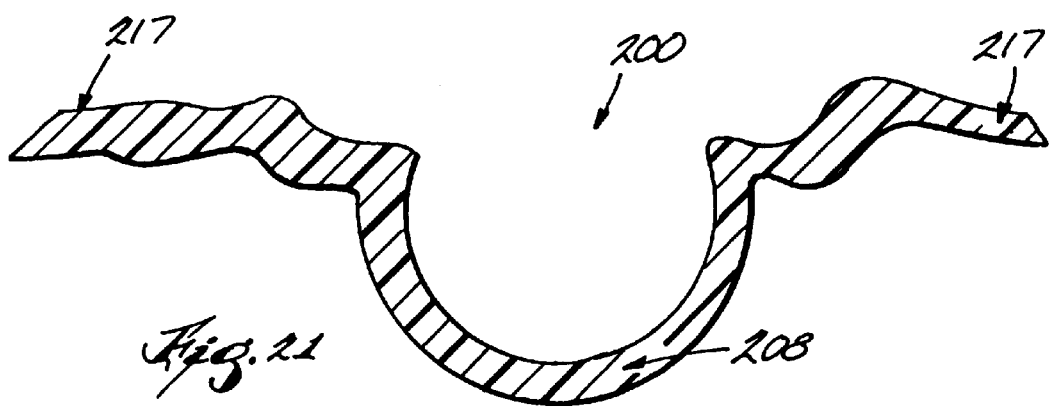
FIG. 21 is an enlarged side section view of the sheet of porous material after formation of the hemispherical distal end geometry.

As FIG. 20 shows, a forming mandrel 206 presses a section 208 of the sheet 200 into the forming cavity 202. The geometry of the forming mandrel 206 matches the hemispherical geometry of the forming cavity 202. The mandrel 206 nests within the cavity 202, sandwiching the material section 208 between them. This sets by pressure the desired hemispherical shape to the material section 208. Either the forming mandrel 206 or the forming cavity 202, or both, may be heated to provide an additional thermal set to the material section 208 within the cavity 202. Pressure and, optionally, heat within the cavity 202 shape the material section 208 from a planar geometry into the desired hemispherical geometry (see FIG. 21).

Figure 22:
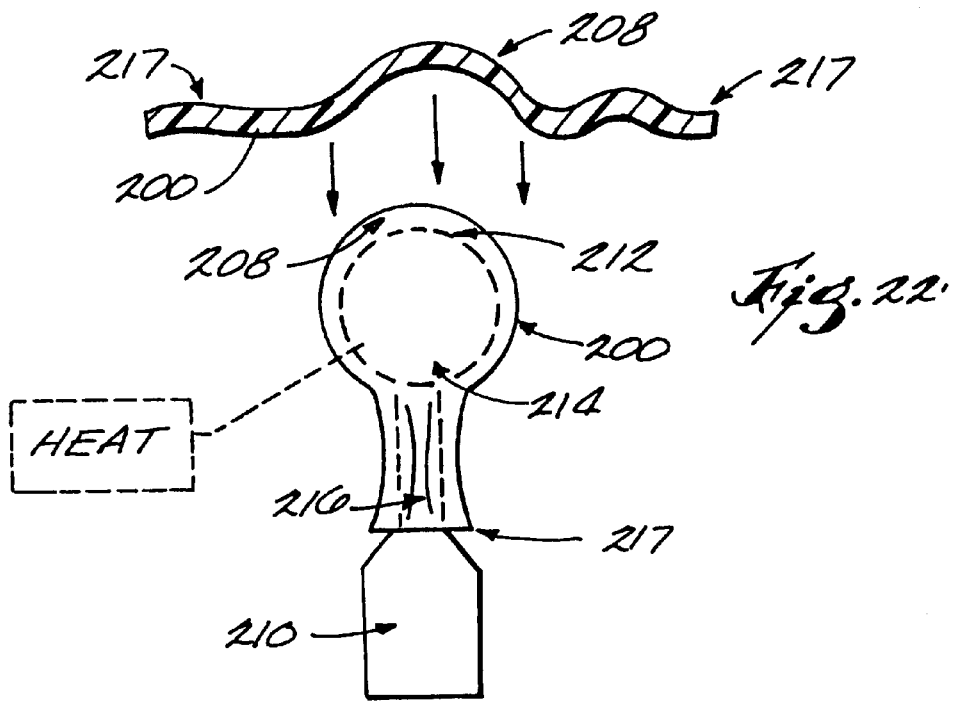
FIG. 22 is a somewhat diagrammatic view of a finishing fixture for forming the hemispherical geometry for the proximal end of the porous electrode body from the preformed sheet shown in FIG. 21.
Figure 23:
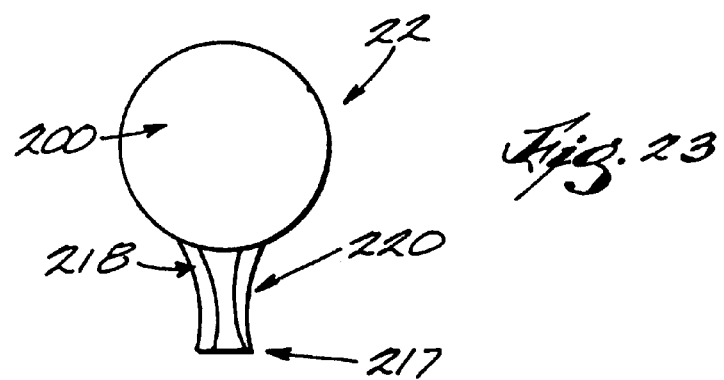
FIG. 23 is an elevation view of the porous electrode body after having been formed by the devices shown in FIGS. 19 to 22.

The sheet with the preformed section 208 is removed from the fixture 204 and mounted upon a finishing fixture 210 (see FIG. 22). The finishing fixture 210 includes a distal end 212 having a geometry that matches the geometry of the preformed section 208. The section 208 fits on the distal fixture end 212.

The finishing fixture 210 includes a proximal end 214 that has the geometry desired for the proximal end of the body 22, which in the illustrated embodiment is hemispherical, too. The sheet 200 is snugly draped about the proximal end 214 of the fixture 210.

The finishing fixture 210 includes a base region 216, about which the remaining material of the sheet 200 is gathered in overlapping pleats 218. The sheet 200 thereby tightly conforms to the entire geometry of the fixture 210.

The finishing fixture 210 may be heated to aid in providing an additional thermal set to the sheet 200 in the desired geometry of the body 22. A clam shell mold (not shown) may also be fastened about the fixture 210 to facilitate the shaping process.

The sheet material, now shaped as the porous body 22 (see FIG. 23) is slipped from the fixture 210. The material pleats 218 that had been gathered about the base region 216 of the fixture 210 are bonded together, for example, by thermal bonding or ultrasonically welding. This forms a reduced diameter neck region 220 in the body 22 to facilitate attachment of the body 22 to the distal end of a catheter tube.

Before pleating, the sheet ends 217 may be cut into sections to minimize the amount of material which accumulates during the pleating process. After pleating, the excess material may be back-folded and bonded to the neck region 220 and/or otherwise trimmed to form a smooth transition between the neck region 220 and the distal region 208.

Figure 24:
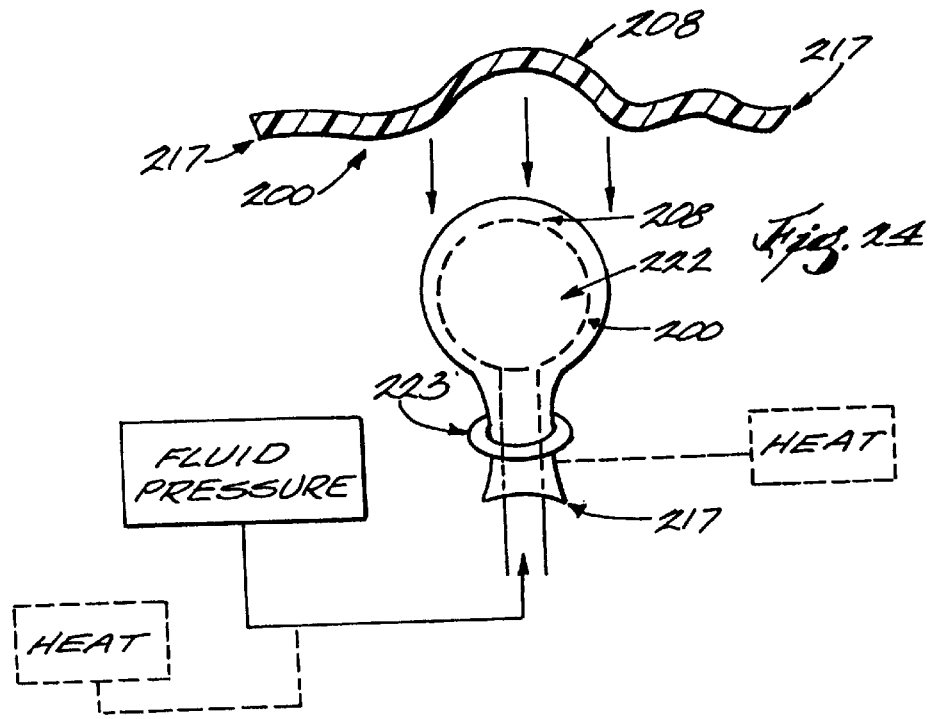
FIG. 24 is a somewhat diagrammatic view of an expandable finishing fixture that can be used instead of the finishing fixture shown in FIG. 22 for forming the hemispherical geometry for the proximal end of the porous electrode body from the preformed sheet shown in FIG. 21.

Alternatively, after removal from the fixture 204, the sheet 200 with preformed section 208, can be wrapped about an expandable fixture 222 (see FIG. 24). The proximal ends 217 of the sheet 200 are snugly tied about the neck of the fixture 222 by a tie member 223.

The fixture 222 comprises a balloon (made, for example, from a Teflon material) or the like, which can be expanded using gas or liquid into the geometry desired for the body 22. The sheet 200 is thereby shaped by the expanding fixture 222 to take the desired geometry.

Before or during expansion of the fixture 222, heat may be applied to the ends 217 of the sheet 200 to soften the material to aid the shaping process. External pressure may also be applied to the proximal ends of the sheet 200 to aid in creating the neck region 220 having the desired reduced diameter. This also helps to prevent "bunching" of material at the proximal ends 217.

The fixture 222 itself may also be heated by using heated gas or liquid to expand the fixture. The heat provides an additional thermal set to the sheet 200 in the desired geometry of the body 22. An external clam shell mold (not shown) may also be fastened about the fixture 222 to facilitate the shaping process. Alternatively, an external shell of a material such as glass, which may be etched away, may be used to impart the desired final geometry.

Throughout any heating process used in forming the body 22 using either fixture 204 or 222, a heat sink (not shown) may be used to cool the preformed distal section 208 so that the pore sizes do not change significantly during a heating process.

Alternatively, the heating effects on the pore size may be estimated and accounted for in forming the sheet 200 in the first instance, before shaping into the body 22. For example, if the pores open during shaping, the pores may be formed during manufacture proportionally smaller, to take into account the increase in size during shaping. Thus, the desired pore size is ultimately achieved while shaping the sheet into the body 22.

Figure 25:
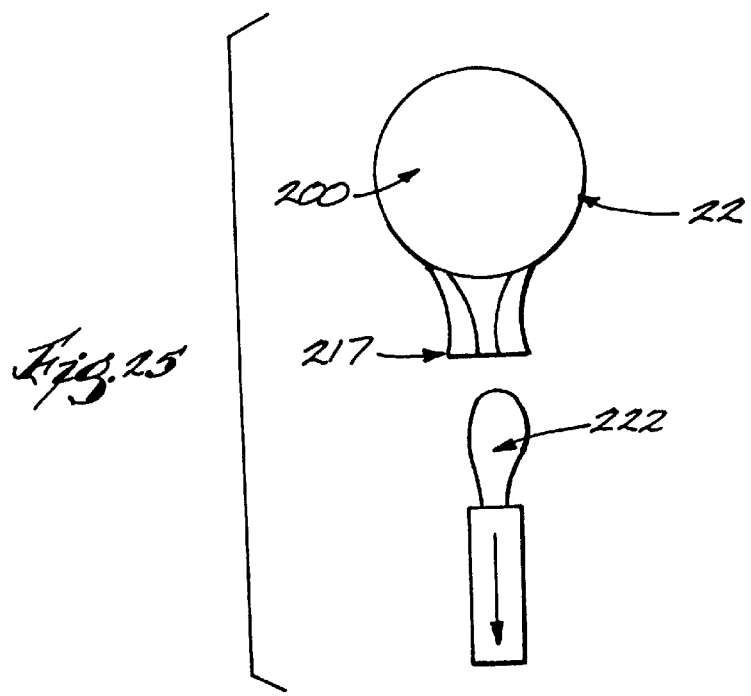
FIG. 25 is an elevation view of the porous electrode body after having been formed by the expandable fixture shown in FIG. 24.

After the shaping process, the fixture 222 is deflated and withdrawn (see FIG. 25). The formed body 22 remains.

In yet another alternative process (see FIGS. 26 and 27), the body 22 can be formed by joining two preformed sections 225 along a circumferential seam 224. In the illustrated embodiment, the sections 225 are formed as hemispheres in the manner shown in FIGS. 19 to 21, with excess material about the periphery of the section 225 cut away. The sections 225 could likewise be preformed by a molding process, depending upon the properties of the material.

The seam 224 joining the two sections 225 is formed through thermal bonding, ultrasonically welding, laser welding, adhesive bonding, sewing, or the like, depending upon the properties of the material. The bonding or sewing method employed is selected to assure that the seam forms an air-tight and liquid-sealed region. The tensile strength of the seam 224 should also exceed the bubble point value of the porous material.

Alternatively, two generally circular planar sections of porous material, cut to size from a sheet, can be joined about their peripheries by a seam, without prior shaping. This creates a normally collapsed disk enclosing an open interior. The introduction of air or liquid into the open interior during use causes the disk to expand into the geometry desired for the body 22. The disk could also enclose an interior support structure 54 (as generally shown in FIGS. 5 to 7), which shapes the disk to the desired geometry.

Preferably, after joining the hemispherical or planar sections 225 at the seam 224, excess material extending beyond to the seam 224 is cut away. Still, as contact between tissue and the somewhat roughened surface region of the seam 224 could cause trauma, the joined sections 225 are preferably everted (see FIG. 28A). Eversion locates the seam 224 within the interior of the body 22 (as FIG. 28B shows), away from direct contact with tissue.

As FIG. 28A shows, the joined sections 225 can be everted by creating a small hole 250 at one end 252, inserting a pull-wire 254 and attaching it to the opposite end 256, then pulling the opposite end 256 through the hole 250. This turns the attached hemispherical sections 225 inside out.

In the foregoing embodiments, the circumferential seam 224 extends about the axis of the body 22. Alternatively (as FIGS. 29A and 29B show), seams 226 can extend along the axis of the body 22 to join two or more sections 228, either planar or preformed into a three dimensional shape, into the body 22. Mating fixtures (not shown) can be used, each carrying a body section 228, to hold the sections 228 stationary while heat or ultrasonic energy is applied to create the seam 226.

As FIG. 30 shows, other axially extending seams 230 may also be placed within a sheet of porous material, not to join the sheet to another sheet, but rather to segment the sheet. Further details about segmented porous electrodes will be discussed later. For the purpose of illustration, FIG. 30 somewhat exaggerates the hemispherical protrusion of the segments along the seams 226 and 230.

Preferably, the resulting body 22 is everted, as just described, to place the axially extending seams 226 or 230 inside the body 22.

It should be appreciated that the sections 225 or 228 shown in FIGS. 26 to 30, whether planar or preforming in three dimensional geometries, need not be made of the same material. Materials of different porous characteristics can be joined by seams in the manner just described. Alternatively, porous materials may be joined by seams to nonporous materials, which can themselves be either electrically conductive or electrically insulating. Or, still alternatively, electrically conductive materials can be joined by seams to insulating materials, to provide double sided electrode bodies, one (electrically conductive) for contacting tissue, and the other (electrically insulating) for exposure to the blood pool. Virtually any flexible material suitable for use in association with an electrode body can be combined using seams according to this aspect of the invention. Also, it should be realized that the number of sections joined together by seams to form a composite electrode body can vary.

Figure 33:
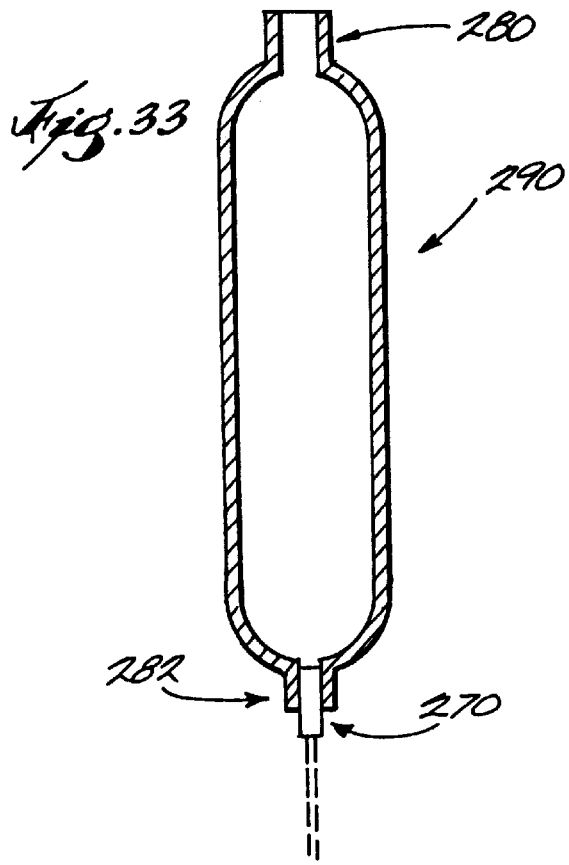
FIG. 33 is an exemplary porous body formed in an elongated, cylindrical geometry with changing radii along its length, forming the distal and proximal neck regions.

Various specific geometries, of course, can be selected, as well. The preferred geometry is essentially spherical and symmetric, with a distal spherical contour, as FIG. 2 shows. However, nonsymmetric or nonspherical geometries can be used. For example, the expandable-collapsible body 22 may be formed with a flattened distal contour, which gradually curves or necks inwardly for attachment with the catheter tube 12. Elongated, cylindrical geometries can also be used, such as shown in FIGS. 33 and 34B, which will be discussed later.

Figure 10:
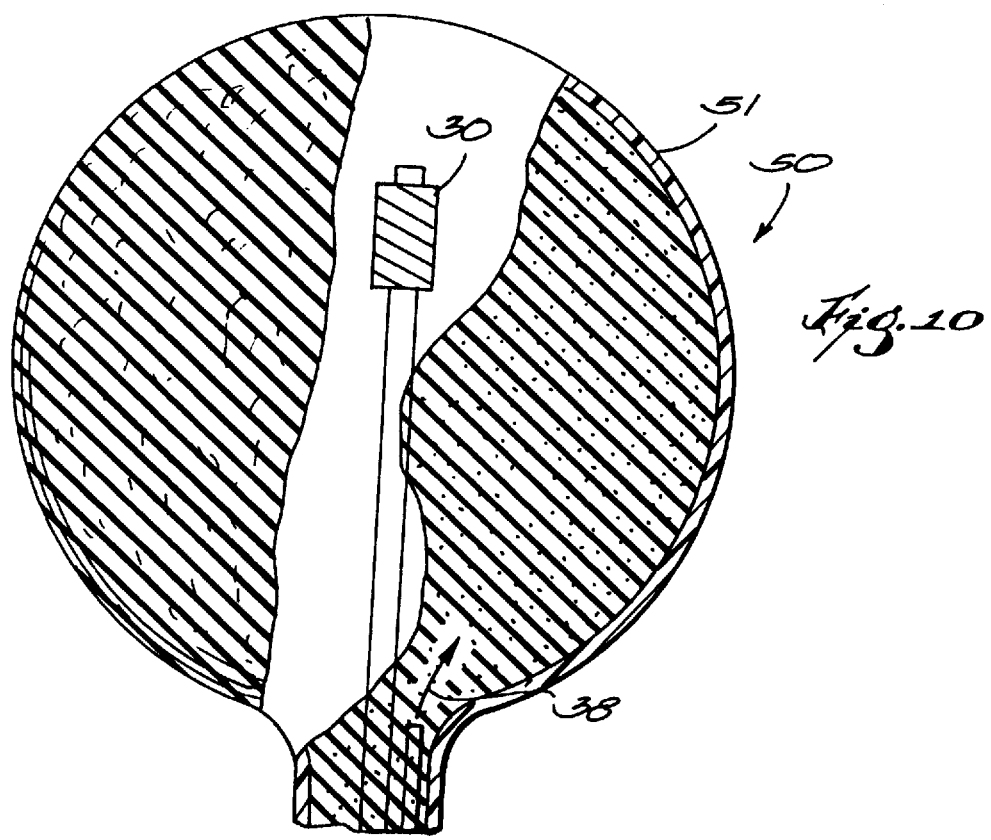
FIG. 10 is an enlarged side elevation view, with portions broken away, of an alternative porous electrode structure usable in association with the system shown in FIG. 1, with the electrode structure comprising a porous foam body shown in its expanded geometry.

FIG. 10 shows an alternative expandable-collapsible porous body 50. In this embodiment, the body 50 comprises open cell foam molded to normally assume the shape of the expanded geometry. The electrode 30 is encapsulated within the foam body 50. The hypertonic liquid medium 38 is introduced into the foam body 50, filling the open cells, to enable the desired ionic transport of ablation energy, as already described. The transport of ions using the foam body 50 will also occur if the body 50 includes an outer porous skin 51 (as the right side of FIG. 10 shows), which can provide a porosity less than the porosity of the foam body 50 to control the perfusion rate.

In this arrangement, a sliding sheath (as previously described) can be advanced along the catheter tube 12 to compress the foam body 50 into the collapsed geometry. Likewise, retraction of the sheath removes the compression force. The foam body 50, free of the sheath, springs open to return the expandable-collapsible body 50 back to the expanded geometry.

In the illustrated and preferred embodiment, a distal steering mechanism 52 (see FIG. 1) enhances the manipulation of the porous electrode structure 20 or 50, both during and after deployment. The steering mechanism 52 can vary. In the illustrated embodiment (see FIG. 1), the steering mechanism 52 includes a rotating cam wheel 56 coupled to an external steering lever 58 carried by the handle 18. The cam wheel 56 holds the proximal ends of right and left steering wires 60. The wires 60 pass with the ablation energy signal wires 32 through the catheter tube 12 and connect to the left and right sides of a resilient bendable wire or leaf spring (not shown) adjacent the distal tube end 16. Further details of this and other types of steering mechanisms are shown in Lundquist and Thompson U.S. Pat. No. 5,254,088, which is incorporated into this Specification by reference.

As shown in FIG. 1, the leaf spring of the steering mechanism 52 is carried within in the distal end 16 of the catheter tube 12. As FIG. 1 shows, forward movement of the steering lever 58 pulls on one steering wire 60 to flex or curve the leaf spring, and, with it, the distal catheter end 16 and the electrode structure 20, in one direction. Rearward movement of the steering lever 58 pulls on the other steering wire 60 to flex or curve the leaf spring 62, and, with it, the distal catheter end 16 and the electrode structure 20, in the opposite direction.

Alternatively, as FIG. 32C shows, a steerable leaf spring 268 is part of a distal fixture 270, which is itself attached to the distal end of the porous body 22. In this arrangement, the leaf spring 268 extends beyond the distal catheter end 16 within a tube 272 inside the porous body 22. The steering wires 60 and 62 attached to the leaf spring 268 also pass through the tube 272. The proximal end of the leaf spring 268 is secured to a hub 274 attached to the distal catheter end 16.

In this arrangement, forward and rearward movement of the steering lever 58 on the handle 18 bends the leaf spring 268 in opposite directions within the body 22. The leaf spring 268 moves the distal fixture 270 and deforms the porous body 22 in the direction that the leaf spring 268 bends.

In either arrangement, the steering mechanism 54 is usable whether the expandable-collapsible body is in its collapsed geometry or in its expanded geometry.

FIGS. 32A and 32B show a preferred way of securing the distal fixture 270 and leaf spring 268 to a porous body 22. In FIG. 32A, the porous body 22 is formed by dipping an expandable fixture 276 having a desired geometry into solution of regenerated cellulose 278. The details of such an expandable fixture 276 have already been described in another context and are shown in FIGS. 24 and 25. It should be appreciated that the porous body 22 can be formed in various other ways, as already described.

As FIG. 32B shows, the fixture forms a dip-formed porous body 22 having a proximal neck region 280 and a distal neck region 282. After molding the body 22, the expandable fixture 276 is collapsed and withdrawn, as FIG. 32B also shows.

As FIG. 32B shows, the distal neck region 282 is secured about the distal fixture 270, for example using adhesive or a sleeve 288 that is secured by adhesive bonding, thermal bonding, mechanical bonding, screws, winding, or a combination of any of these.

The distal fixture 270 has, preattached to it, the leaf spring 268 and associated components, already described. When initially secured to the fixture 270, the proximal neck region 280 of the body 22 is oriented in a direction opposite to the leaf spring 268.

After securing the distal neck region 282 to the fixture 270, the body 22 is everted about the distal fixture 270 over the leaf spring 268, as FIG. 32C shows. The proximal end of the leaf spring 268 is secured to the hub 274 carried by the distal catheter end 16. The everted proximal neck region 280 is then secured to the distal catheter end by use of a sleeve 286. The sleeve 286 can be secured about the catheter tube in various ways, including adhesive bonding, thermal bonding, mechanical bonding, screws, winding, or a combination of any of these.

Various alternative ways of attaching a porous electrode body to the distal end of a catheter are disclosed in copending patent application entitled "Stem Elements for Securing Tubing and Electrical Wires to Expandable-Collapsible Electrode Structures," (Attorney Docket 2458A-6).

As will be described in greater detail later, the distal fixture 270 can also serve as a nonporous electrically conductive region on the porous body 22. Similar fixtures 270 can be located elsewhere on the porous body 22 for the same purpose.

A stilette (not shown) may also be attached to the distal fixture 270 instead of or in combination with the leaf spring 268. From there, the stilette extends inside the body 22 (following eversion), through the catheter tube 12, to a suitable push-pull controller on the handle 18 (not shown). The stilette is movable along the axis of the catheter tube 12 to push and pull axially upon the distal fixture 270, thereby elongating or shortening the body 22.

Further details concerning the attachment of a distal fixture to an electrode body are shown in copending patent application entitled "Expandable-Collapsible Electrode Structures With Distal End Steering or Manipulation," (Attorney Docket 2458A-4).

Figure 34A:
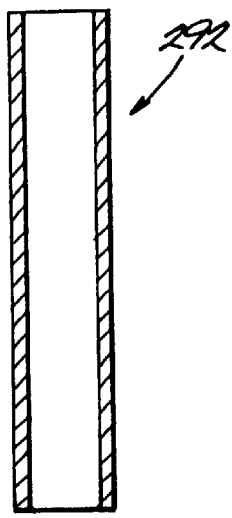
FIG. 34A is another exemplary porous body formed as a tube in an elongated, cylindrical geometry with constant radii along its length.
Figure 34B:
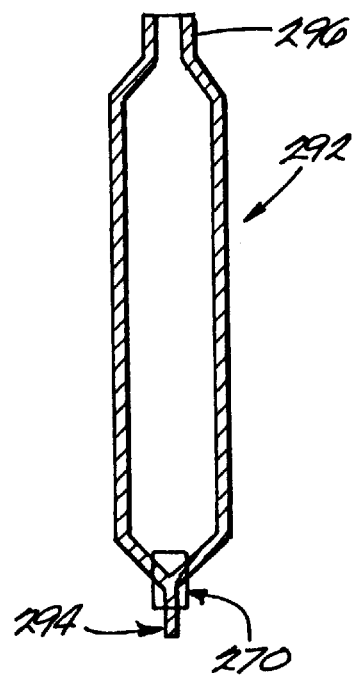
FIG. 34B is the tube shown in FIG. 34A, with its distal end closed by a seam, and a port tube sealed to its proximal end for attachment to a catheter tube.

FIGS. 33 and 34A/34B show exemplary electrode bodies having elongated, cylindrical geometries, which can be associated with various distal fixtures in the manner shown and attached to distal catheter ends 16 in the manner shown in FIGS. 32B and 32C.

In FIG. 33, the body 290 is formed by extrusion, dipping, or molding into an elongated geometry with varying radii to form the distal and proximal neck regions 280 and 282. A suitable distal fixture 270 (shown in phantom lines) can be secured within the distal neck region 282 and the elongated body 22 everted to complete the assembly, in the manner shown in FIGS. 32B and 32C. The proximal neck region 280 can then be secured to a distal catheter end 16 in the manner shown in FIG. 32C.

In FIGS. 34A and 34B, the body 22 is formed from a tube 292 of material formed by extrusion, molding, or dipping with a uniform radius (shown in FIG. 34A). In this arrangement (see FIG. 34B), a seam 294, formed the manner previously disclosed, closes the distal end of the tube 292. The proximal end of the tube 292 is sealed about a tubular port 296, for attachment to the distal catheter end 16. Alternatively, the distal end of the tube 292 can be sealed about a distal fixture 270 (shown in phantom lines in FIG. 34B). In the latter case, the tube 292 is everted about the distal fixture 270 before attachment to the catheter distal end 16.

The pattern of pores 44 that define the porous region of the body may vary. Preferably, as generally shown in FIGS. 2 and 3, the region of at least the proximal ⅓rd surface of the expandable-collapsible body 22 is free of pores 44.

The absence of pores 44 on the at least proximal ⅓rd surface of the expandable-collapsible body 22 is desirable for several reasons. This region is not normally in contact with tissue, so the presence of the virtual electrode boundary serves no purpose. Furthermore, this region also presents the smallest diameter. If electrically conductive, this region would possess the greatest current density, which is not desirable. Keeping the proximal region of smallest diameter, which is usually free of tissue contact, free of pores 44 assures that the maximum current density will be distributed at or near the distal region of the expandable-collapsible body 22, which will be in tissue contact.

When it is expected that ablation will occur with the distal region of body 22 oriented in end-on contact with tissue, the porous region should, or course, be oriented about the distal tip of the expandable-collapsible body 22. For this end-on orientation, the porous region may comprise a continuous cap deposited upon the distal ⅓rd to ½ of the body 22, as FIGS. 2 and 3 show. However, when distal contact with tissue is contemplated, the preferred embodiment (see FIG. 11) segments the electrically conductive porous region into separate energy transmission zones 62 arranged in a concentric "bulls eye" pattern about the distal tip of the body 22.

When it is expected that ablation will occur with the side region of the body 22 oriented in contact with tissue, the porous region is preferably segmented into axially elongated energy transmission zones 62 (see FIG. 12), which are circumferentially spaced about the distal ⅓rd to ½ of the body.

Figure 13:
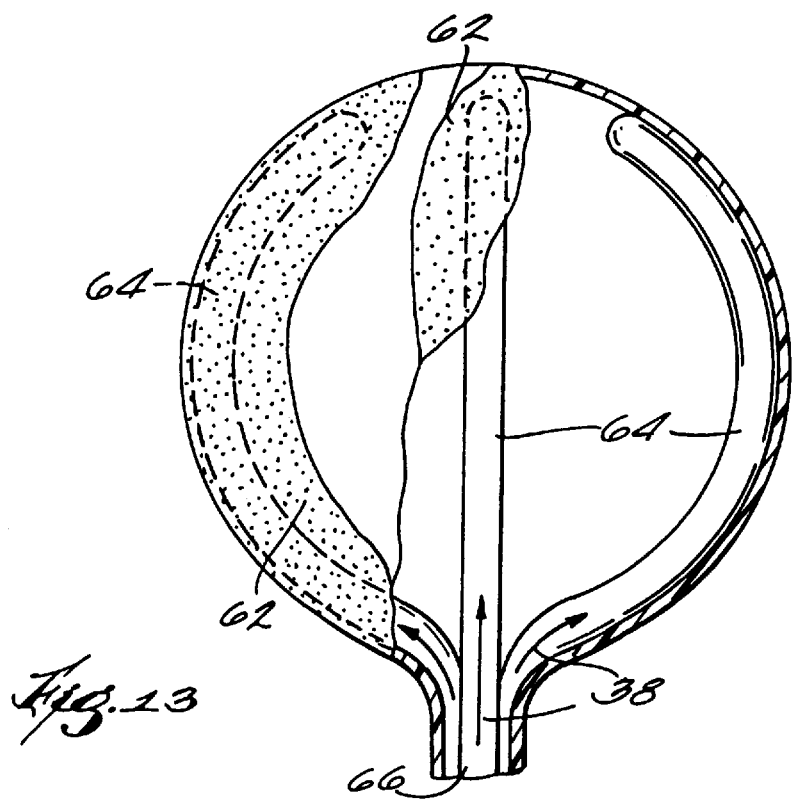
FIG. 13 is a side view, with portions broken away, showing the use of multiple chambers to convey liquid to the segmented pore regions shown in FIG. 12.

When the porous region comprises segmented zones 62 on the body 22, an interior group of sealed bladders 64 (see FIG. 13) can be used to individually convey liquid 38 to each porous region segment 62. Each bladder 64 individually communicates with a lumen 66 to receive the electrically conductive liquid for the one porous region 62 it services. The multiple lumens pass through the catheter tube 12. The multiple bladders 64 also provide the ability to more particularly control the geometry of the expanded body 22, by selectively inflating with the liquid some but not all the bladders 64.

The bladders 64 may be separately formed and inserted into the body 22, or they may be integrally formed during molding the main expandable-collapsible body 22.

Figure 12:
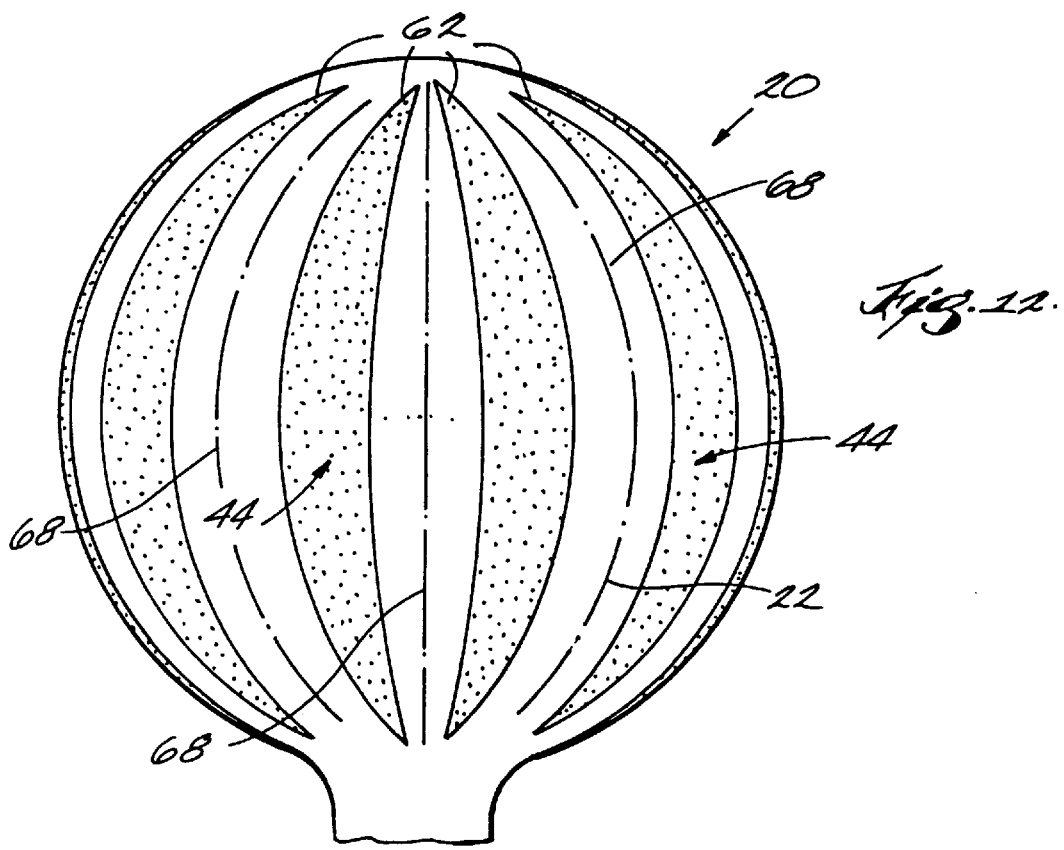
FIG. 12 is an enlarged side view of a porous electrode structure usable in association with the system shown in FIG. 1, with the pores of the structure arranged in circumferentially spaced segments along the side of the body.

As FIG. 12 shows, segmented porous zones 62 are also well suited for use in association with folding expandable-collapsible bodies 22. In this arrangement, the regions that are free of pores comprise creased or folding regions 68. To create these regions 68, the mold for the body 22 has a preformed surface geometry such that the expandable-collapsible material would be formed slightly thinner, indented, or ribbed along the desired regions 68. The expandable-collapsible body 22 collapses about these creased regions 68, causing the body 22 to circumferentially fold upon itself in a consistent, uniform fashion. The resulting collapsed geometry can thus be made more uniform and compact.

It should be appreciated that the foldable body 22 shown in FIG. 12 can also be used for other patterns of porous regions. The creased regions 68 can also be provided with pores, if desired.

Figure 14:
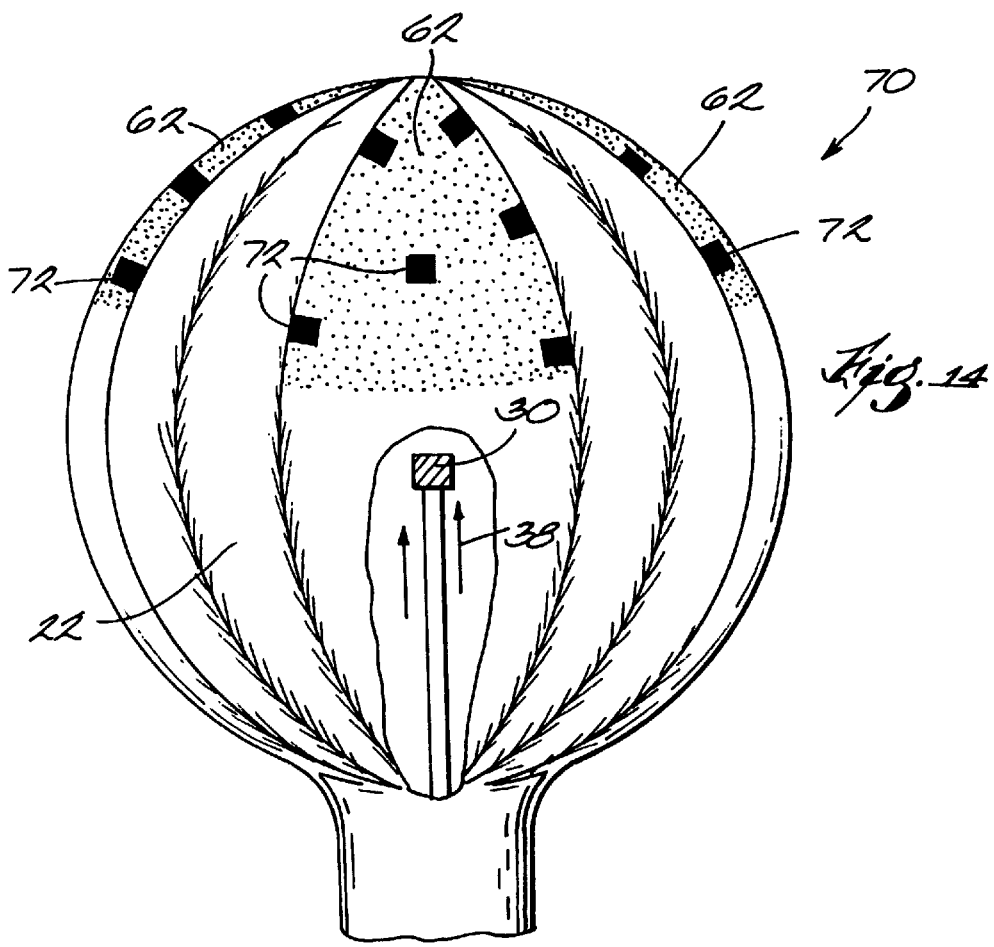
FIG. 14 is an enlarged side elevation view, with portions broken away, of a porous electrode structure usable in association with the system shown in FIG. 1, which also carries nonporous electrode elements.

FIG. 14 shows an embodiment of an expandable-collapsible electrode structure 70 that serves dual functions. The structure 70 includes an expandable-collapsible body 22, as previously described, containing the interior electrode 30. The body 22 contains an electrically conductive fluid 38, and also includes one or more porous regions 62 to enable ionic transport of electrical energy, also as just described.

The structure 70 shown in FIG. 14 also includes one or more nonporous, electrically conductive regions 72 on the surface of the body 22. In one embodiment (as FIG. 14 shows), the nonporous conductive regions 72 comprise metal, such as gold, platinum, platinum/iridium, among others, deposited upon the expandable-collapsible body 22 by sputtering, vapor deposition, ion beam deposition, electroplating over a deposited seed layer, or a combination of these processes. Alternatively, the nonporous conductive regions 72 can comprise thin foil affixed to the surface of the body. Still alternatively, the nonporous conductive regions can comprise solid fixtures (like the distal fixture 270 shown in FIG. 32C) carried by the porous body 22 at or more locations. Signal wires (not shown) within the body are electrically coupled to the nonporous regions. The signal wires traverse the catheter tube 12 for coupling to the connectors 38 carried by the handle 18.

Figure 15:
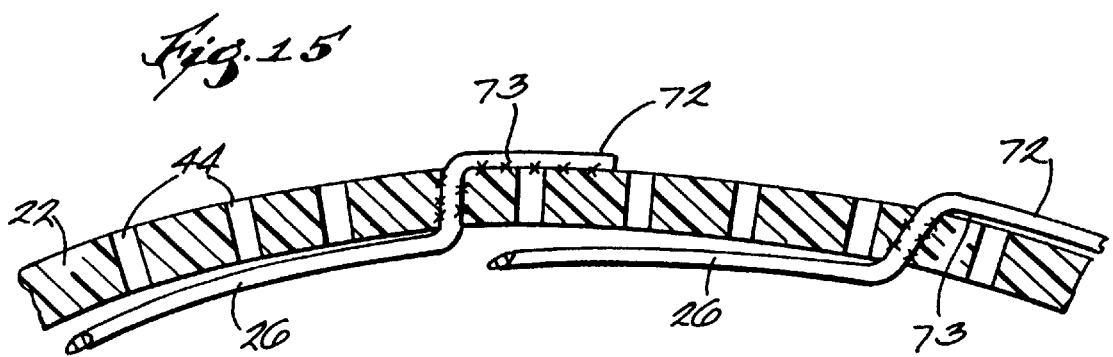
FIG. 15 is an enlarged side section view of a porous electrode structure, which also carries electrode elements formed by wire snaked through the body of the structure.

In the preferred embodiment (see FIG. 15), the nonporous conductive regions 72 comprise insulated signal wires 26 passed into the interior of the body and then snaked through the body 22 at the desired point of electrical connection. The electrical insulation of the distal end of the snaked-through wire 26 is removed to exposed the electrical conductor, which is also preferably flattened, to serve as the conductive region 72. The flattened region 72 is affixed by an electrically conductive adhesive 73 to body 22. Adhesive 73 is also preferable applied in the region of the body 22 where the wire 26 passes to seal it. The same signal wire 26 can be snaked through the body 22 multiple times to establish multiple regions 72, if desired.

Various ways for attaching nonporous electrodes 72 and associated signal wires to an expandable-collapsible electrode body 22 are described in copending Patent Application entitled "Enhanced Electrical Connections for Electrode Structures" (Attorney Docket 2458A-5).

The nonporous regions 72 can be used to sense electrical activity in myocardial tissue. The sensed electrical activity is conveyed to an external controller, which processes the potentials for analysis by the physician. The processing can create a map of electrical potentials or depolarization events for the purpose of locating potential arrhythmia foci. Once located with the nonporous regions 72, the porous regions 62 can be used to convey radio frequency energy as previously described to ablate the foci.

Alternatively, or in combination with sensing electrical activities, the nonporous regions 72 can be used to convey pacing signals. In this way, the nonporous regions can carry out pace mapping or entrainment mapping.

Figure 16:
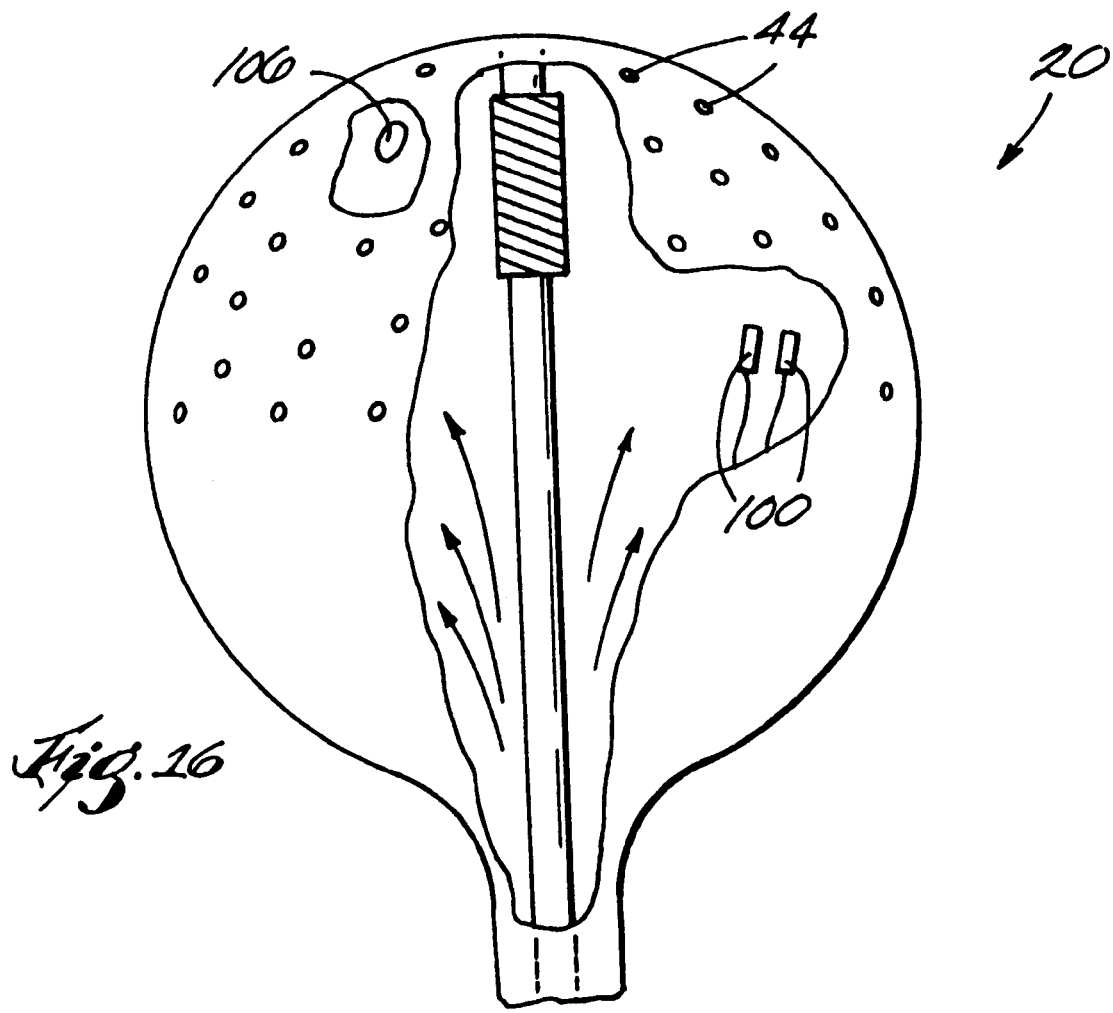
FIG. 16 is an enlarged side elevation view, with portions broken away, of a porous electrode structure with interior pacing/sensing electrodes.

Preferably (see FIGS. 16), the interior surface of the body 22 carries electrodes 100 suitable for unipolar or bipolar sensing or pacing. Although these electrodes 100 are located on the interior surface of the body 22, their ability for sensing or pacing is not impaired because of the good electrical conductive properties of the body 22.

Different electrode placements can be used for unipolar or bipolar sensing or pacing. For example, pairs of 2-mm length and 1-mm width electrodes 100 can be deposited on the interior surface of the body 22. Connection wires 102 can be attached to these electrodes 100. To prevent the hypertonic solution from electrically short-circuiting these electrodes, they have to be covered with an electrically insulating material 104 (e. g. epoxy, adhesive etc.). Preferably the interelectrode distance is about 1 mm to insure good quality bipolar electrograms. Preferred placements of these interior electrodes are at the distal tip and center of the structure 22. Also, when multiple zones are used, it is desired to have the electrodes 100 placed in between the ablation regions.

It is also preferred to deposit opaque markers 106 on the interior surface of the body 22 so that the physician can guide the device under fluoroscopy to the targeted site. Any high-atomic weight material is suitable for this purpose. For example, platinum, platinum-iridium. can be used to build the markers 106. Preferred placements of these markers 106 are at the distal tip and center of the structure 22.

The expandable-collapsible structure 70 shown in FIG. 14 thereby combines the use of "solid" nonporous electrodes 72 with "liquid" or porous electrodes 62. The expandable-collapsible structure makes possible the mapping of myocardial tissue for therapeutic purposes using one electrode function, and the ablation of myocardial tissue for therapeutic purposes using a different electrode function.

In an alternative embodiment, the nonporous regions 72 of the structure 70 can be used in tandem with the porous regions 62 to convey radio frequency energy to ablate tissue. In this arrangement, the signal wires serving the region 72 are electrically coupled to the generator 40 to convey radio frequency energy for transmission by one or more regions 72. At the same time, the interior electrode 30 receives radio frequency energy for transmission by the medium 38 through the porous body. The ionic transport across the porous structure surrounding the regions 72 extends the effective surface area of the ablation electrode.

In this embodiment, the expandable-collapsible structure 70 shown in FIG. 14 thereby combines the use of electrodes 72 having a first effective surface area for sensing and mapping. The first effective surface area can be selectively increased for ablation purposes by ionic transport of a hypertonic liquid across a porous structure surrounding the electrodes 72.

If liquid perfusion occurs through the pores, an interior electrode 30 is not required to increase the effective electrode surface area of the regions. The liquid perfusion of the ionic medium through the pores at the time the regions transmit radio frequency energy is itself sufficient to increase the effective transmission surface area of the regions 72. However, if ionic transfer occurs without substantial liquid perfusion, it is believed that it would be advantageous in increasing the effective surface area to also transmit radio frequency energy using an interior electrode 30 at the same time that radio frequency is being delivered to the exterior regions 72 for transmission.

It should also be appreciated that, in this embodiment, the regions 72 can themselves be made from a porous, electrically conducting material. In this way, ionic transport can occur across the regions 72 themselves.

As before described (see FIG. 1), a controller 32 preferably governs the conveyance of radio frequency ablation energy from the generator 30 to the electrode carried within the body 22. In the preferred embodiment (see FIG. 2), the porous electrode structure 20 carries one or more temperature sensing elements 104, which are coupled to the controller 32.

The temperature sensing elements 104 can take the form of thermistors, thermocouples, or the equivalent. The sensing elements 104 are in thermal conductive contact with the exterior of the electrode structure 20 to sense conditions in tissue outside the structure 20 during ablation.

Temperatures sensed by the temperature sensing elements 104 are processed by the controller 32. Based upon temperature input, the controller adjusts the time and power level of radio frequency energy transmissions by the electrode 30, to achieve the desired lesion patterns and other ablation objectives.

Various ways for attaching temperature sensing elements to an expandable-collapsible electrode body are described in copending Patent Application entitled "Enhanced Electrical Connections for Electrode Structures" (Attorney Docket 2458A-5).

As FIGS. 31A, 31B, and 31C show, temperature sensing elements 104 can also be positioned proximal to or within a seam 258 joining sheets 260 and 262 of porous material together into a body 22. The formation of such seams 258 has been already described and is also shown in FIGS. 26 to 30.

As shown in FIGS. 31A and 31B, each temperature sensing element 104 is placed on one sheet 260, and then covered by the other sheet 262. The two sheets 260 and 262 are then seamed together, forming the body 22. The seam 258 encapsulates the sensing elements. The signal wire 264 for each sensing element 104 extends free of the seam 258 to the exterior of the sheets 260 and 262, as FIGS. 31A and 31B show.

As previously described, the body 22 is preferably everted (see FIG. 28A). As FIG. 31C shows, eversion locates both the seam 258 and the encapsulated signal wires 264 within the interior of the body 22. The signal wires 264 are passed through the neck 266 for coupling to the controller 32.

Instead of or in addition to the temperature sensing elements 104, pacing electrodes or sensing electrodes may be encapsulated within the seams 258 of everted electrode bodies 22 in the manner shown in FIGS. 31A to 31C. In such arrangements, it is preferred to locate the electrodes so that, after eversion, they are located within the seams close to the surface of the material where intended contact between the body material and tissue is to take place.

Further details of the use of multiple ablation energy transmitters controlled using multiple temperature sensing elements are disclosed in copending U.S. patent application Ser. No. 08/286,930, filed Aug. 8,1994, and entitled "Systems and Methods for Controlling Tissue Ablation Using Multiple Temperature Sensing Elements".

EXAMPLE 1

In Vitro Analysis

Three electrode configurations were analyzed:

(1) a porous expandable-collapsible electrode structure made according to the invention, having a 13 mm disk-shaped body constructed from dialysis tubing made from regenerated cellulose(manufactured by Spectra), with a molecular weight cut off of 12,000–14,000 Daltons, and using 9% saline solution as the internal liquid medium;

(2) a sputtered platinum disk-shaped electrode body having a diameter of 13 mm; and (3) an expandable-collapsible hemispherical electrode structure constructed of aluminum foil with a diameter of 10 mm.

A thermistor was embedded 0.5 mm into animal tissue (sheep) at the region where maximum temperature conditions existed. For electrodes (1) and (2), the maximum temperature was at edges of the disk-shaped body, due to edge heating effects. For the electrode (3), the maximum temperature was at the distal tip of the hemispherical body, where current densities are greatest.

Radio frequency electromagnetic power was regulated to maintain the thermistor temperature at 60° C., 70° C., 80° C., or 90° C. All lesion dimensions were measured based on the 60° C. isotherms, marking the discoloration of tissue.

The following Table 2 lists the observed in vitro results.

TABLE 2

| Electrode | Time (Sec) | Average Power (Watts) | Average Impedance (Ohms) | Average Temp (° C.) | Lesion Depth (mm) | Lesion Length (mm) |
|---|---|---|---|---|---|---|
| 1 | 120 | 11 | 75 | 59 | 4.2 | 15.8 |
| 1 | 120 | 21 | 72 | 68 | 6.4™ | 17.5 |
| 1 | 120 | 17 | 69 | 78 | 8.0 | 17.1 |
| 1 | 120 | 15 | 62 | 78 | 9.7™ | 18.3 |
| 1 | 120 | 25 | 69 | 87 | 8.9™ | 19.5 |
| 1 | 120 | 26 | 66 | 87 | 8.8™ | 20.8 |
| 1 | 120 | 22 | 69 | 88 | 10.0™ | 19.1 |
| 2 | 128 | 9 | 76 | 78 | 6.3 | 14.2 |
| 3 | 120 | 23 | 69 | 78 | 6.0 | 13.7 |
| 3 | 120 | 37 | 55 | 86 | 7.4 | 18.5 |

Note: TM indicates that the lesion was transmural, so depths were actually larger than measured.

The porous electrode structure (1) was minimally affected by convective cooling compared to normal metal ablation electrode, such as electrode (2). This was observed by varying fluid flow about the electrode during a particular lesion and observing that, with a porous electrode structure, no change in power was required to maintain thermistor temperature.

Table 2 shows that the porous electrode structure created lesions at least as large as a metal coated electrode structures when regulating power based on tissue temperature. The porous electrode structure also had reasonable impedance levels compared to the metal coated electrode structures.

This Example demonstrates that a porous electrode structure can create lesions deeper than 1.0 cm in a controlled fashion to ablate epicardial, endocardial, or intramural VT substrates.

The dialysis tubing forming the porous electrode structure has a high water adsorption characteristic. The dialysis tubing becomes significantly more flexible when exposed to water. The molecular weight cutoff was 12,000 to 14,000 daltons. Larger or smaller molecular weight cut-offs are available from Spectrum. The conversion from molecular weight cutoff to estimated pore size for the dialysis tubing tested is 100,000 daltons equals 0.01 μm; 50,000 daltons equals 0.004 μm; 10,000 daltons equals 0.0025 μm; 5,000 daltons equals 0.0015 μm, as taken from Spectrum Medical Instruments brochure entitled "Dialysis/Ultrafiltration," 94/95 (p 10).

The dialysis tubing possesses a hydrophilic nature and high porosity despite low pore sizes. As a result, the bubble point value is extremely high and the resistivity is low enough to not require fluid flow during delivery of radiofrequency energy.

EXAMPLE 2

Finite Element Analysis

A three-dimensional finite element model was created for a porous electrode structure having a body with an elongated shape, with a total length of 28.4 mm, a diameter of 6.4 mm, and a body wall thickness of 0.1 mm. A 0.2-mm diameter metal wire extended within the length of the body to serve as an interior electrode connected to an RF energy source. The body was filled with 9% hypertonic solution, having an electrical resistivity of 5.0 ohm·cm. The porous body of the structure was modeled as an electric conductor. Firm contact with cardiac tissue was assumed along the entire length of the electrode body lying in a plane beneath the electrode. Contact with blood was assumed along the entire length of the electrode body lying in a plane above the electrode. The blood and tissue regions had resistivities of 150 and 500 ohm·cm, respectively.

Analyses were made based upon resistivities of 1.2 k-ohm·cm and 12 k-ohm·cm for the electrode body.

Table 3 shows the depth of the maximum tissue temperature when RF ablation power is applied to the porous electrode at various power levels and at various levels of resistivity for the porous body of the electrode.

TABLE 3

| Resistivity of the Porous Body (k-ohm · cm) | Power (Watts) | Time (Sec) | Maximum Tissue Temp (° C.) | Depth of Maximum Tissue Temp (cm) |
| --- | --- | --- | --- | --- |
| 1.2 | 58 | 120 | 96.9 | 1.1 |
| 1.2 | 58 | 240 | 97.9 | 1.4 |
| 12 | 40 | 120 | 94.4 | 0.8 |
| 12 | 40 | 240 | 95.0 | 1.0 |

Figure 17:
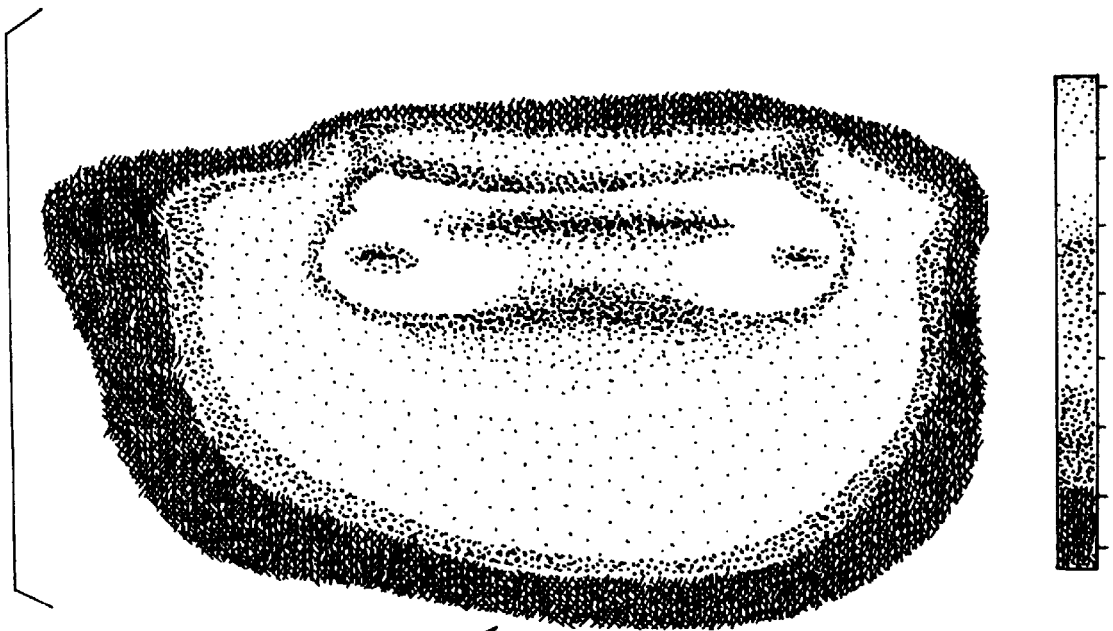
FIGS. 17 and 18 are diagrammatic representations of the tissue temperature profiles associated with a porous electrode structure when operated under different conditions.

FIG. 17 shows the temperature profiles when power is applied to the electrode at 58 watts for 240 seconds when the porous body has a resistivity of 1.2 k-ohm·cm. The depth of 50° C. isotherm in FIG. 17 is 1.4 cm.

Figure 18:
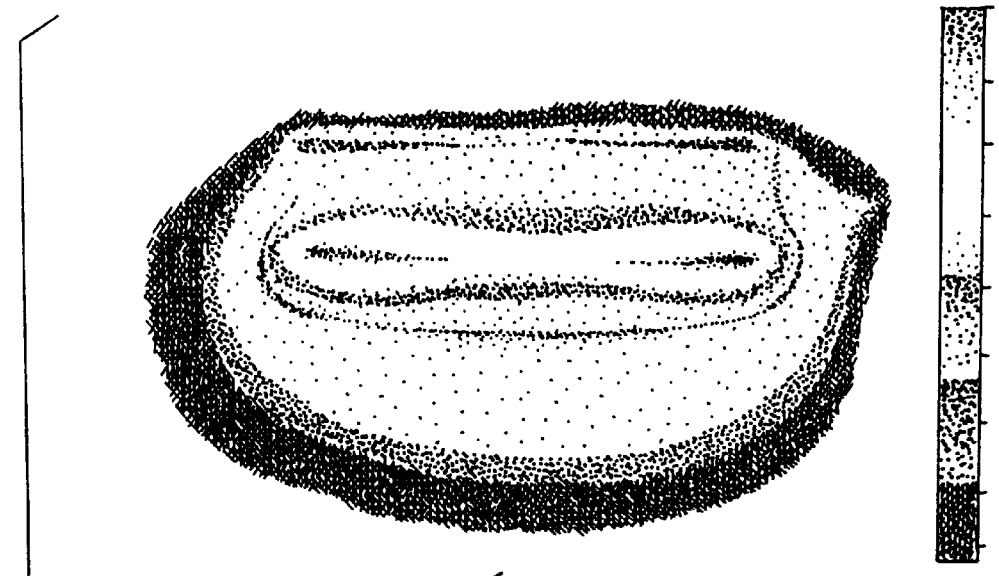

FIG. 18 shows the temperature profiles when power is applied to the electrode at 40 watts for 240 seconds when the porous body has a resistivity of 12 k-ohm·cm. Depth of 50° C. isotherm in FIG. 18 is 1.0 cm.

In all cases, the maximal temperature is located at the interface between tissue and the opposite end edges of the elongated porous structure. This dictates that the preferred location for temperature sensing elements for an elongated geometry of the porous body is at each end edge of the body. Preferably, each edge should carry at least one temperature sensing element, and multiple sensing elements should be located in diametrically opposite sides to assure that at least one of them faces tissue.

The data also show that the hottest region is not moved deep into the tissue, as would be observed with metal surface electrodes. The hottest region consistently resides at the tissue-electrode body interface for direct sensing. This feature reduces the difference between sensed temperature and actual hottest tissue temperature potentially to a theoretical 0° C., although somewhat higher differentials may be encountered given other aspects of the instrumentation.

The porous electrode body with higher resistivity body (see FIG. 18) generated more uniform temperature profiles, compared to a porous body having the lower resistivity value (see FIG. 17). Due to additional heating generated at the tissue-electrode body interface with increased electrode body resistivity, less power was required to reach same maximal temperature. The consequence was that the lesion depth decreased.

As before explained, by selecting the resistivity of the body 22, the physician can significantly influence lesion geometry. The use of a low-resistivity body 22 results in deeper lesions, and vice versa. The following Table 4, based upon empirical data, demonstrates the relationship between body resistivity and lesion depths.

TABLE 4

| Resistivity (ohm · cm) | Power (Watts) | Temperature (° C.) | Lesion Depth (cm) | Time (sec) |
| --- | --- | --- | --- | --- |
| 850 | 94 | 97 | 1.2 | 120 |
| 1200 | 58 | 97 | 1.1 | 120 |
| 12,000 | 40 | 95 | 0.8 | 120 |

Because of the reduced thermal conductivity of the porous electrode structure, when compared to nonporous, metallic surface electrodes, lesion formation is expected to be less sensitive to dynamic blood flow conditions around the electrode. The application of ablation energy through porous electrodes can be more closely controlled to obtain desired lesion characteristics, particularly when shallow atrial lesion are desired.

The following Table 5, based upon empirical data, demonstrates the reduced sensitivity of porous electrode structures to convective cooling conditions due to changes in blood flow rates.

TABLE 5

| Convective Cooling Conditions | Maximum Temperature (° C.) | Power (Watts) | Lesion Depth (cm) |
| --- | --- | --- | --- |
| Normal | 97 | 94 | 1.2 |
| 50% Reduced | 98 | 94 | 1.3 |
| 75% Reduced | 95 | 79 | 0.8 |

The use of porous electrode structures provides structural benefits. It isolates possible adherence problems that may be associated with the placement of metal, electrically conductive shells to the outside of expandable-collapsible bodies. Porous electrode structures also avoid potential problems that tissue sticking to exterior conductive materials could create.

In addition to these structural benefits, the temperature control of the ablation process is improved. When using a conventional metal electrode to ablate tissue, the tissue-electrode interface is convectively cooled by surrounding blood flow. Due to these convective cooling effects, the region of maximum tissue temperature is located deeper in the tissue. As a result, the temperature conditions sensed by sensing elements associated with metal electrode elements do not directly reflect actual maximum tissue temperature. In this situation, maximum tissue temperature conditions must be inferred or predicted from actual sensed temperatures. Using a porous electrode structure 20 or 70, convective cooling of the tissue-electrode interface by the surrounding blood flow is minimized. As a result, the region of maximum temperature is located at the interface between tissue and the porous electrode. As a result, the temperature conditions sensed by sensing elements associated with porous electrode elements will more closely reflect actual maximum tissue.

EXAMPLE 3

In Vitro experiments were performed to compare hydrophilic materials (Hphl) versus hydrophobic materials (HPhb) in terms of their use as porous tissue ablation elements. Table 6 summarizes the results.

to selectively form lesions that are either wide and shallow or large and deep. Various methodologies can be used to control the application of radio frequency energy to achieve this result.

A. $D_{50C}$ Function

In one representative embodiment, the controller 42 includes an input 300 (see FIG. 1) for receiving from the physician a desired therapeutic result in terms of (i) the extent to which the desired lesion should extend beneath the tissue-electrode interface to a boundary depth between viable and nonviable tissue and/or (ii) a maximum tissue temperature developed within the lesion between the tissue-electrode interface and the boundary depth.

The controller 42 also includes a processing element 302 (see FIG. 1), which retains a function that correlates an observed relationship among lesion boundary depth, ablation power level, ablation time, actual sub-surface tissue temperature, and electrode temperature. The processing element 302 compares the desired therapeutic result to the function and selects an operating condition based upon the comparison to achieve the desired therapeutic result without exceeding a prescribed actual or predicted sub-surface tissue temperature.

The operating condition selected by the processing element 302 can control various aspects of the ablation procedure, such as controlling the ablation power level, limiting the ablation time to a selected targeted ablation time, limiting the ablation power level subject to a prescribed maximum ablation power level, and/or the orientation of the porous region 44 of the body 22, including

TABLE 6

Summary of Porous Ablation Materials

| Mat'l | Mfgr | HPhb | HPhl | Pore Size | Bubble point value | No Flow Impedance | Impedance w/ Flow | Mat'l Brkdwn | Lesion Depth |
|---|---|---|---|---|---|---|---|---|---|
| Dialysis Tubing | Spectrum | | ✓ | .025 μm | High | 87 Ω | 87 Ω | No | 13.8 mm |
| Nylon Mesh | Spectrum | | ✓ | 5 μm | Med | 68 Ω | 68 Ω | No | 9.9 mm |
| Stain-St Mesh | Spectrum | | | 30 μm | Low | 67 Ω | 67 Ω | No | 9.7 mm |
| Polycarb Film | Millipore | | ✓ | 1.2 μm | High 14 psi | 78 Ω | 78 Ω | No | 11.6 mm |
| Polyvinylidene Fluoride | Millipore | ✓ | | 5 μm | High | >300 Ω | 84 Ω | Yes | 10.7 mm w/ flow |
| PTFE | Millipore | ✓ | | 5 μm | High | >300 Ω | >300 Ω | N/A | NONE |
| Polyethersulfone | Gelman | | ✓ | 5 μm | Med 1–6 psi | 80 Ω | 80 Ω | No | 10.6 mm |
| Polyethersulfone | Gelman | | ✓ | 0.1 μm | High | >300 Ω | >300 Ω | N/A | NONE |
| Modified Acrylic copolymer | Gelman | ✓ | | 10 μm | Med 1–6 psi | 68 Ω | 68 Ω | Yes | 9.9 mm |
| Modified Acrylic copolymer | Gelman | ✓ | | 5 μm | High | >300 Ω | 70 Ω | Yes | 11.0 mm w/ flow |
| Modified Acrylic w/ backing | Gelman | ✓ | | 10 μm | High | >300 Ω | 61 Ω | Yes | 11.3 mm w/ flow |
| PTFE | Pore Tech | ✓ | | 1 μm | High | >300 Ω | >300 Ω | N/A | NONE |
| Cellulose Acetate | Goodfellow | | ✓ | Very low | High | >300 Ω | >300 Ω | N/A | NONE |

Note: "Mat'l Brkdwn" refers to the presence of material breakdown, as described above.

Table 6 demonstrates that pore sizes may be decreased using hydrophilic materials, thereby minimizing or stopping liquid perfusion through the porous material, while still enabling ionic transport through the membrane.

Hydrophobic porous materials make possible the realization of high resistivity porous electrodes. On the other hand, hydrophilic porous materials make possible the realization of low resistivity porous electrodes.

Obtaining Desired Lesion Characteristics

As the foregoing tables demonstrate, the same expandable-collapsible porous electrode structure 20 is able prescribing a desired percentage contact between the region 44 and tissue. The processing element 302 can rely upon temperature sensors carried by or otherwise associated with the expandable-collapsible structure 20 that penetrate the tissue to sense actual maximum tissue temperature. Alternatively, the processing element 302 can predict maximum tissue temperature based upon operating conditions.

In the preferred embodiment, the electrode structure 20 carries at least one temperature sensing element 104 to sense instantaneous localized temperatures (T1) of the thermal mass of the region 44. The temperature T1 at any given time is a function of the power supplied to the electrode 30 by the generator 40.

The characteristic of a lesion can be expressed in terms of the depth below the tissue surface of the 50° C. isothermal region, which will be called $D_{50C}$. The depth $D_{50C}$ is a function of the physical characteristics of the porous region 44 (that is, its electrical and thermal conductivities, resistivities, and size); the percentage of contact between the tissue and the porous region 44; the localized temperature T1 of the thermal mass of the region 44; the magnitude of RF power (P) transmitted by the interior electrode 30, and the time (t) the tissue is exposed to the RF power.

For a desired lesion depth $D_{50C}$, additional considerations of safety constrain the selection of an optimal operating condition among the operating conditions listed in the matrix. The principal safety constraints are the maximum tissue temperature TMAX and maximum power level PMAX.

The maximum temperature condition TMAX lies within a range of temperatures which are high enough to provide deep and wide lesions (typically between about 85° C. and 95° C.), but which are safely below about 100° C., at which tissue desiccation or tissue micro-explosions are known to occur. It is recognized that TMAX will occur a distance below the electrode-tissue interface between the interface and $D_{50C}$.

The maximum power level PMAX takes into account the physical characteristics of the interior electrode 30 and the power generation capacity of the RF generator 40.

These relationships can be observed empirically and/or by computer modeling under controlled real and simulated conditions, as the foregoing examples illustrate. The $D_{50C}$ function for a given porous region 44 can be expressed in terms of a matrix listing all or some of the foregoing values and their relationship derived from empirical data and/or computer modeling.

The processing element 302 includes in memory this matrix of operating conditions defining the $D_{50C}$ temperature boundary function, as described above for t=120 seconds and TMAX=95° C. and for an array of other operating conditions.

The physician also uses the input 300 to identify the characteristics of the structure 20, using a prescribed identification code; set a desired maximum RF power level PMAX; a desired time t; and a desired maximum tissue temperature TMAX.

Based upon these inputs, the processing element 302 compares the desired therapeutic result to the function defined in the matrix. The generator 42 selects an operating condition to achieve the desired therapeutic result without exceeding the prescribed TMAX by controlling the function variables.

This arrangement thereby permits the physician, in effect, to "dial-a-lesion" by specifying a desired $D_{50C}$.

Further details of deriving the $D_{50C}$ function and its use in obtaining a desired lesion pattern are found in copending U.S. application Ser. No. 08/431,790, filed May 1, 1995, entitled "Systems and Methods for Obtaining Desired Lesion Characteristics While Ablating Body Tissue," which is incorporated herein by reference.

B. Segmented Regions: Duty Cycle Control

Figure 11:
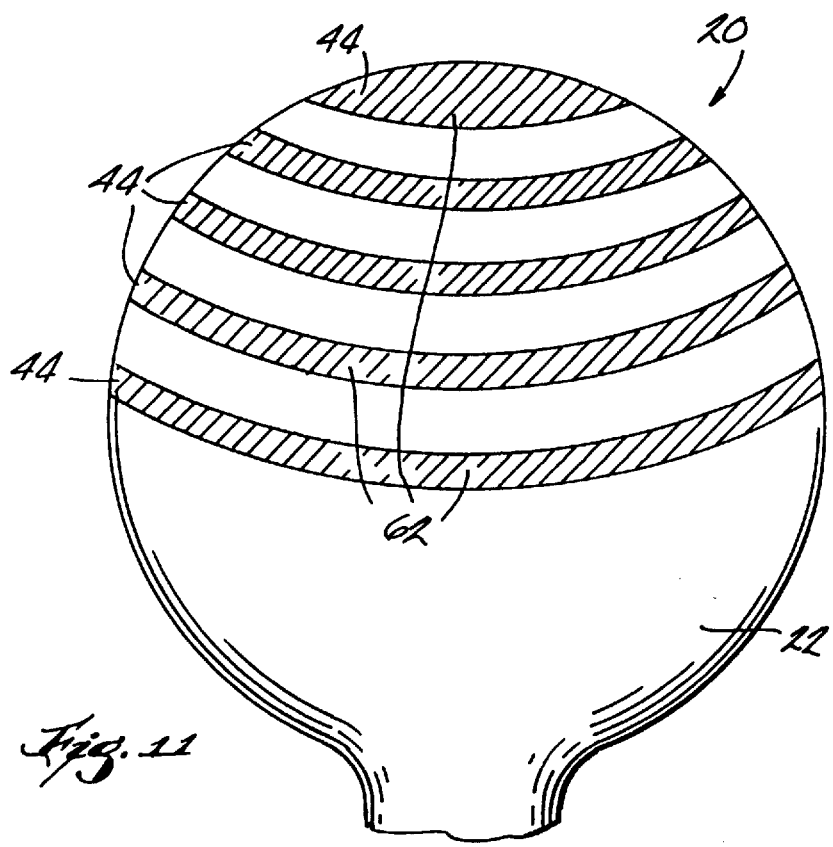
FIG. 11 is an enlarged side view of a porous electrode structure usable in association with the system shown in FIG. 1, with the pores of the structure arranged in a bulls eye pattern on the distal end of the body.

Various RF energy control schemes can also be used in conjunction with segmented porous patterns shown in FIG. 11 (the axially spaced, bull's-eye pattern of zones) and FIG. 12 (the circumferentially spaced zones) For the purpose of discussion, the porous zones 44 (which will also be called electrode regions) will be symbolically designated E(J), where J represents a given zone 44 (J=1 to N).

As before described, each electrode region E(J) has at least one temperature sensing element 104, which will be designated S(J,K), where J represents the zone and K represents the number of temperature sensing elements on each zone (K=1 to M).

In this mode, the generator 40 is conditioned through an appropriated power switch interface to deliver RF power in multiple pulses of duty cycle 1/N.

With pulsed power delivery, the amount of power ($P_{E(J)}$) conveyed to each individual electrode region E(J) is expressed as follows:

$$P_{E(J)} \alpha AMP_{E(J)}^2 \times DUTYCYCLE_{E(J)}$$

where:
  $AMP_{E(J)}$ is the amplitude of the RF voltage conveyed to the electrode region E(J), and
  $DUTYCYCLE_{E(J)}$ is the duty cycle of the pulse, expressed as follows:

$$DUTYCYCLE_{E(J)} = \frac{TON_{E(J)}}{TON_{E(J)} + TOFF_{E(J)}}$$

where:
  $TON_{E(J)}$ is the time that the electrode region E(J) emits energy during each pulse period,
  $TOFF_{E(J)}$ is the time that the electrode region E(J) does not emit energy during each pulse period.

The expression $TON_{E(J)}+TOFF_{E(J)}$ represents the period of the pulse for each electrode region E(J).

In this mode, the generator 40 can collectively establish duty cycle ($DUTYCYCLE_{E(J)}$) of 1/N for each electrode region (N being equal to the number of electrode regions).

The generator 40 may sequence successive power pulses to adjacent electrode regions so that the end of the duty cycle for the preceding pulse overlaps slightly with the beginning of the duty cycle for the next pulse. This overlap in pulse duty cycles assures that the generator 40 applies power continuously, with no periods of interruption caused by open circuits during pulse switching between successive electrode regions.

In this mode, the temperature controller 42 makes individual adjustments to the amplitude of the RF voltage for each electrode region ($AMP_{E(J)}$), thereby individually changing the power $P_{E(J)}$ of ablating energy conveyed during the duty cycle to each electrode region, as controlled by the generator 40.

In this mode, the generator 40 cycles in successive data acquisition sample periods. During each sample period, the generator 40 selects individual sensors S(J,K), and temperature codes TEMP(J) (highest of S(J,K)) sensed by the sensing elements 104, as outputted by the controller 42.

When there is more than one sensing element 104 associated with a given electrode region (for example, when edge-located sensing elements are used, the controller 42 registers all sensed temperatures for the given electrode region and selects among these the highest sensed temperature, which constitutes TEMP(J).

In this mode, the generator 40 compares the temperature TEMP(J) locally sensed at each electrode E(J) during each data acquisition period to a set point temperature $TEMP_{SET}$ established by the physician. Based upon this comparison, the generator 40 varies the amplitude $AMP_{E(J)}$ of the RF voltage delivered to the electrode region E(J), while maintaining the $DUTYCYCLE_{E(J)}$ for that electrode region and all other electrode regions, to establish and maintain TEMP (J) at the set point temperature $TEMP_{SET}$.

The set point temperature TEMP SET can vary according to the judgment of the physician and empirical data. A representative set point temperature for cardiac ablation is believed to lie in the range of 40° C. to 95° C., with 70° C. being a representative preferred value.

The manner in which the generator 40 governs $AMP_{E(J)}$ can incorporate proportional control methods, proportional integral derivative (PID) control methods, or fuzzy logic control methods.

For example, using proportional control methods, if the temperature sensed by the first sensing element TEMP(1) >$TEMP_{SET}$, the control signal generated by the generator 30 individually reduces the amplitude $AMP_{E(1)}$ of the RF voltage applied to the first electrode region E(1), while keeping the duty cycle $DUTYCYCLE_{E(1)}$ for the first electrode region E(1) the same. If the temperature sensed by the second sensing element TEMP(2)<$TEMP_{SET}$, the control signal of the generator 30 increases the amplitude $AMP_{E(2)}$ of the pulse applied to the second electrode region E(2), while keeping the duty cycle $DUTYCYCLE_{E(2)}$ for the second electrode region E(2) the same as $DUTYCYCLE_{E(1)}$, and so on. If the temperature sensed by a given sensing element is at the set point temperature $TEMP_{SET}$, no change in RF voltage amplitude is made for the associated electrode region.

The generator 40 continuously processes voltage difference inputs during successive data acquisition periods to individually adjust $AMP_{E(J)}$ at each electrode region E(J), while keeping the collective duty cycle the same for all electrode regions E(J). In this way, the mode maintains a desired uniformity of temperature along the length of the ablating element.

Using a proportional integral differential (PID) control technique, the generator takes into account not only instantaneous changes that occur in a given sample period, but also changes that have occurred in previous sample periods and the rate at which these changes are varying over time. Thus, using a PID control technique, the generator will respond differently to a given proportionally large instantaneous difference between TEMP (J) and $TEMP_{SET}$, depending upon whether the difference is getting larger or smaller, compared to previous instantaneous differences, and whether the rate at which the difference is changing since previous sample periods is increasing or decreasing.

Further details of individual amplitude/collective duty cycle control for segmented electrode regions based upon temperature sensing are found in copending U.S. application Ser. No. 08/439,824, filed May 12, 1995 and entitled "Systems and Methods for Controlling Tissue Ablation Using Multiple Temperature Sensing Elements," which is incorporated herein by reference.

C. Segmented Regions: Differential Temperature Disabling

In this control mode, the controller 42 selects at the end of each data acquisition phase the sensed temperature that is the greatest for that phase ($TEMP_{SMAX}$). The controller 42 also selects for that phase the sensed temperature that is the lowest ($TEMP_{SMIN}$)

The generator compares the selected hottest sensed temperature $TEMP_{SMAX}$ to a selected high set point temperature $TEMP_{HISET}$. The comparison generates a control signal that collectively adjusts the amplitude of the RF voltage for all electrode regions using proportional, PID, or fuzzy logic control techniques.

In a proportion control implementation scheme:
(i) If $TEMP_{SMAX}$>$TEMP_{HISET}$, the control signal collectively decreases the amplitude of the RF voltage delivered to all regions;
(ii) If $TEMP_{SMAX}$<$TEMP_{HISET}$, the control signal collectively increases the amplitude of the RF voltage delivered to all regions:
(iii) If $TEMP_{SMAX}$=$TEMP_{HISET}$, no change in the amplitude of the RF voltage delivered to all regions.

It should be appreciated that the generator can select for amplitude control purposes any one of the sensed temperatures $TEMP_{SMAX}$, $TEMP_{SMIN}$, or temperatures in between, and compare this temperature condition to a preselected temperature condition.

The generator governs the delivery of power to the regions based upon difference between a given local temperature TEMP (J) and $TEMP_{SMIN}$. This implementation computes the difference between local sensed temperature TEMP(J) and $TEMP_{SMIN}$ and compares this difference to a selected set point temperature difference $\Delta TEMP_{SET}$. The comparison generates a control signal that governs the delivery of power to the electrode regions.

If the local sensed temperature TEMP(J) for a given electrode region E(J) exceeds the lowest sensed temperature $TEMP_{SMIN}$ by as much as or more than $\Delta TEMP_{SET}$ (that is, if TEMP(J)–$TEMP_{SMIN} \geq \Delta TEMP_{SET}$) the generator turns the given region E(J) off. The generator turns the given region E(J) back on when TEMP(J)–$TEMP_{SMIN}$<$\Delta TEMP_{SET}$.

Alternatively, instead of comparing TEMP(J) and $TEMP_{SMIN}$, the generator can compare $TEMP_{SMAX}$ and $TEMP_{SMIN}$. When the difference between $TEMP_{SMAX}$ and $TEMP_{SMIN}$ equals or exceeds a predetermined amount $\Delta TEMP_{SET}$, the generator turns all regions off, except the region where $TEMP_{SMIN}$ exists. The generator 30 turns these regions back on when the temperature difference between $TEMP_{SMAX}$ and $TEMP_{SMIN}$ is less than $\Delta TEMP_{SET}$.

Further details of the use of differential temperature disabling are found in copending U.S. patent application Ser. No. 08/286,930, filed Aug. 8, 1994, and entitled "Systems and Methods for Controlling Tissue Ablation Using Multiple Temperature Sensing Elements," which is incorporated herein by reference.

D. PID Control

With porous electrode structures, the minimal effects of convective cooling by the blood pool enables the use of actual sensed temperature conditions as maximum tissue temperature TMAX, instead of predicted temperatures. Because of this, such structures also lend themselves to the use of a proportional integral differential (PID) control technique. An illustrative PID control techniques usable in association with these electrode structures are disclosed in copending U.S. Pat. application Ser. No. 08/266,023, filed Jun. 27, 1994, entitled "Tissue Heating and Ablation Systems and Methods Using Time-Variable Set Point Temperature Curves for Monitoring and Control."

Finally, it should be appreciated that interior electrodes 30 located within porous expandable-collapsible bodies can be used for mapping myocardial tissue within the heart. In this use, the interior electrodes sense electrical activity in the heart, which can take the form, for example, of electrical potentials or tissue resistivity. The sensed electrical activity is conveyed to an external controller, which processes the sensed activities for analysis by the physician.

It should further be appreciated that interior electrodes 30 located within porous expandable-collapsible bodies can be used alternatively, or in combination with sensing electrical activities, to convey pacing signals. In this way, the interior electrodes 30 can carry out pace mapping or entrainment mapping.

Various features of the invention are set forth in the following claims.

We claim:

1. A porous electrode assembly for heating body tissue comprising a wall having an exterior peripherally surrounding an interior area, a lumen for conveying a medium containing ions into the interior area, and an element for electrically coupling the medium within the interior area to a source of electrical energy, wherein at least a portion of the wall comprises a porous material sized to block passage of macromolecules while allowing passage of ions contained in the medium to thereby enable ionic transport of electrical energy sufficient to heat tissue through the porous material to the exterior of the wall.

2. A porous electrode assembly for heating body tissue comprising a wall having an exterior peripherally surrounding an interior area, a medium containing ions filling the interior area and subject to internal pressure, and an element for electrically coupling the medium to a source of electrical energy, wherein at least a portion of the wall comprises a porous material sized to pass ions contained in the medium without substantial liquid perfusion through the porous material, to thereby enable ionic transport of electrical energy sufficient to heat tissue through the porous material to the exterior of the wall.

3. A porous electrode assembly for heating body tissue comprising a wall having an exterior peripherally surrounding an interior area, a medium containing ions filling the interior area and subject to internal pressure, and an element for electrically coupling the medium to a source of electrical energy, wherein at least a portion of the wall comprises a porous material sized to pass ions contained in the medium to thereby enable ionic transport of electrical energy sufficient to heat tissue through the porous material to the exterior of the wall, the porous material having a bubble point value greater than the internal pressure.

4. A porous electrode assembly for heating body tissue comprising a wall having an exterior peripherally surrounding an interior area, a medium containing ions filling the interior area and subject to internal pressure, and an element for electrically coupling the medium to a source of electrical energy, wherein at least a portion of the wall comprises a hydrophilic porous material sized to pass ions contained in the medium to thereby enable ionic transport of electrical energy sufficient to heat tissue through the porous material to the exterior of the wall, the porous material having a bubble point value greater than the internal pressure, whereby ionic transport occurs substantially free of liquid perfusion through the porous material.

5. A porous electrode assembly according to claim 1 or 2 or 3 or 4 wherein the porous material comprises an ultrafiltration membrane.

6. A porous electrode assembly according to claim 1 or 2 or 3 or 4 wherein the element comprises an electrically conductive electrode in the interior area of the wall.

7. An assembly according to claim 6, wherein the electrically conductive electrode comprises a noble metal.

8. An assembly according to claim 6 wherein the electrically conductive electrode includes a material selected from the group consisting essentially of gold, platinum, platinum/iridium, 4and combinations thereof.

9. An assembly according to claim 1, wherein the electrode assembly includes the medium containing ions, and the medium comprises a hypertonic solution.

10. An assembly according to claim 9 wherein the hypertonic solution includes sodium chloride.

11. An assembly according to claim 10 wherein the sodium chloride is present in a concentration at or near saturation.

12. An assembly according to claim 10 wherein the sodium chloride is present in a concentration of up to about 9% weight by volume.

13. An assembly according to claim 9 wherein the hypertonic solution includes potassium chloride.

14. An assembly according to claim 2 or 3 or 4, wherein the medium has a resistivity lower than about 150 ohm cm.

15. An assembly according to claim 2 or 3 or 4, wherein the medium has a resistivity lower than about 10 ohm cm.

16. An assembly according to claim 2 or 3 or 4, wherein the medium has a resistivity of about 5 ohm cm.

17. An assembly according to claim 2 or 3 or 4, wherein the medium carries a radiopaque substance.

18. An assembly according to claim 1 or 2 or 3 or 4 wherein the porous material has an electrical resistivity of at least about 500 ohm·cm.

19. An assembly according to claim 1 or 2 or 3 or 4 wherein the porous material has an electrical resistivity less than about 500 ohm·cm.

20. An assembly according to claim 1 or 2 or 3 or 4 wherein at least a portion of the wall includes an electrically conductive material.

21. An assembly according to claim 20 wherein the electrically conductive material of the wall is porous.

22. An assembly according to claim 20 wherein the electrically conductive material of the wall is nonporous.

23. An assembly according to claim 20 wherein the electrically conductive material comprises a coating deposited on the wall.

24. An assembly according to claim 20 wherein the electrically conductive material comprises foil affixed to the wall.

25. An assembly according to claim 20
wherein the electrically conductive material is located in the wall.

26. An assembly according to claim 20
wherein the electrically conductive material comprises noninsulated signal wire exposed on the exterior of the wall.

27. An electrode assembly according to claim 20
wherein at least a portion of the wall is free of electrically conductive material.

28. An electrode assembly according to claim 1 or 2 or 3 or 4
wherein at least a portion of the wall is free of electrically conductive material.

29. An assembly according to claim 1 or 2 or 3 or 4
and further including members assembled within the interior area to form a support structure underlying the wall.

30. An assembly according to claim 29
wherein the support members are made from metal material.

31. An assembly according to claim 30
wherein the metal material includes nickel titanium.

32. An assembly according to claim 30
wherein the metal material includes stainless steel.

33. An assembly according to claim 29
wherein the support members are made from plastic material.

34. An assembly according to claim 29
wherein the support members comprise elongated spline elements assembled in a circumferentially spaced relationship.

35. An assembly according to claim 29
wherein the support members comprise a porous foam structure.

36. An assembly according to claim 1 or 2 or 3 or 4
wherein the wall includes a distal region and a proximal region, and
wherein the porous material occupies more of the distal region than the proximal region.

37. An assembly according to claim 36
wherein at least ⅓rd of the proximal region is free of porous material.

38. An assembly according to claim 36
wherein the porous material occupies at least ⅓rd of the distal region.

39. An assembly according to claim 1 or 2 or 3 or 4
and further including a radiopaque material carried by the assembly.

40. A porous electrode assembly according to claim 2
wherein at least one temperature sensing element is carried by the wall in thermal conductive contact with the exterior of the wall.

41. A porous electrode assembly according to claim 2
wherein the porous material comprises a microporous membrane.

42. A porous electrode assembly according to claim 2
wherein at least a portion of the wall includes an electrically conductive material that is a coextruded part of the wall.

43. A system for heating body tissue, comprising:
a catheter tube having a distal end;
a return electrode;
a fluid source of a medium containing ions;
an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area, an electrically conductive element in the interior area;
a source of energy; and
means for coupling the electrically conductive element and the return electrode to the source of energy to transmit the energy,
wherein at least a portion of the wall comprises a porous material sized to block passage of macromolecules while allowing passage of ions contained in the medium, thereby allowing ionic transport of electrical energy from the electrically conductive element through the medium to the exterior of the wall for transmission to the return electrode to heat tissue located between the return electrode and the electrode.

44. A system for ablating body tissue, comprising:
a catheter tube having a distal end;
a return electrode;
a fluid source of a medium containing ions;
an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area, and an electrically conductive element in the interior area;
a source of energy; and
means for coupling the electrically conductive element and the return electrode to the source of energy to transmit the energy,
wherein at least a portion of the wall comprises a porous material sized to block passage of macromolecules while allowing passage of ions contained in the medium, thereby allowing ionic transport of electrical energy from the electrically conductive element through the medium to the exterior of the wall for transmission to the return electrode to ablate tissue located between the return electrode and the electrode.

45. A system for ablating heart tissue, comprising:
a catheter tube having a distal end for deployment in a heart chamber;
a return electrode;
a fluid source of a medium containing ions;
an electrode on the distal end of the catheter tube adapted to be electrically coupled to the return electrode through heart tissue, the electrode comprising a wall having an exterior peripherally surrounding an interior area, a lumen for conveying the medium containing ions from the fluid source into the interior area, and an electrically conductive element in the interior area;
a source of energy; and
means for coupling the electrically conductive element and the return electrode to the source of energy to transmit the energy,
wherein at least a portion of the wall comprises a porous material sized to block passage of macromolecules while allowing passage of ions contained in the medium, thereby allowing ionic transport of electrical energy from the electrically conductive element through the medium to the exterior of the wall for transmission to the return electrode to ablate heart tissue located between the return electrode and the electrode.

46. A system for heating body tissue, comprising:

a catheter tube having a distal end;

a return electrode;

a fluid source of a medium containing ions;

an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area, and an electrically conductive element in the interior area;

a source of energy; and means for coupling the electrically conductive element and the return electrode to the source of energy to transmit the energy, wherein at least a portion of the wall comprises a porous material sized to pass ions contained in the medium without substantial liquid perfusion through the porous material, thereby allowing ionic transport of electrical energy from the electrically conductive element through the medium to the exterior of the wall for transmission to the return electrode to heat tissue located between the return electrode and the electrode.

47. A system for ablating body tissue, comprising:

a catheter tube having a distal end;

a return electrode;

a fluid source of a medium containing ions;

an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area, and an electrically conductive element in the interior area;

a source of energy; and means for coupling the electrically conductive element and the return electrode to the source of energy to transmit the energy, wherein at least a portion of the wall comprises a porous material sized to pass ions contained in the medium without substantial liquid perfusion through the porous material, thereby allowing ionic transport of electrical energy from the electrically conductive element through the medium to the exterior of the wall for transmission to the return electrode to ablate tissue located between the return electrode and the electrode.

48. A system for ablating heart tissue, comprising:

a catheter tube having a distal end for deployment in a heart chamber;

a return electrode;

a fluid source of a medium containing ions;

an electrode on the distal end of the catheter tube adapted to be electrically coupled to the return electrode through heart tissue, the electrode comprising a wall having an exterior peripherally surrounding an interior area, a lumen for conveying the medium containing ions from the fluid source into the interior area, and an electrically conductive element in the interior area;

a source of energy; and means for coupling the electrically conductive element and the return electrode to the source of energy to transmit the energy, wherein at least a portion of the wall comprises a porous material sized to pass ions contained in the medium without substantial liquid perfusion through the porous material, thereby allowing ionic transport of electrical energy from the electrically conductive element through the medium to the exterior of the wall for transmission to the return electrode to ablate heart tissue located between the return electrode and the electrode.

49. A system for heating body tissue, comprising:

a catheter tube having a distal end;

a return electrode;

a fluid source of a medium containing ions;

an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area, subject to internal pressure, and an electrically conductive element in the interior area;

a source of energy; and means for coupling the electrically conductive element and the return electrode to the source of energy to transmit the energy, wherein at least a portion of the wall comprises a porous material sized to pass ions contained in the medium, thereby allowing ionic transport of electrical energy from the electrically conductive element through the medium to the exterior of the wall for transmission to the return electrode to heat tissue located between the return electrode and the electrode, the porous material having a bubble point value greater than the internal pressure.

50. A system for ablating body tissue, comprising:

a catheter tube having a distal end;

a return electrode;

a fluid source of a medium containing ions;

an electrode on the distal end of the catheter tube adapted to be electrically coupled to the return electrode through tissue, the electrode comprising a wall having an exterior peripherally surrounding an interior area, a lumen for conveying the medium containing ions from the fluid source into the interior area subject to an internal pressure, and an electrically conductive element in the interior area;

a source of energy; and means for coupling the electrically conductive element and the return electrode to the source of energy to transmit the energy, wherein at least a portion of the wall comprises a porous material sized to pass ions contained in the medium, thereby allowing ionic transport of electrical energy from the electrically conductive element through the medium to the exterior of the wall for transmission to the return electrode to ablate tissue located between the return electrode and the electrode, the porous material having a bubble point value greater than the internal pressure.

51. A system for ablating heart tissue, comprising:

a catheter tube having a distal end for deployment in a heart chamber;

a return electrode;

a fluid source of a medium containing ions;

an electrode on the distal end of the catheter tube adapted to be electrically coupled to the return electrode through heart tissue, the electrode comprising a wall having an exterior peripherally surrounding an interior area, a lumen for conveying the medium containing ions from the fluid source into the interior area subject to an internal pressure, and an electrically conductive element in the interior area;

a source of energy; and means for coupling the electrically conductive element and the return electrode to the source of energy to transmit the energy, wherein at least a portion of the wall comprises a porous material sized to pass ions contained in the medium, thereby allowing ionic transport of electrical energy from the electrically conductive element through the medium to the exterior of the wall for transmission to the return electrode to ablate heart tissue located between the return electrode and the electrode, the porous material having a bubble point value greater than the internal pressure.

52. A system according to claim 43 or 44 or 45 or 46 or 47 or 48 or 49 or 50 or 51 wherein the medium comprises a hypertonic solution.

53. A system according to claim 52 wherein the hypertonic solution includes sodium chloride.

54. A system according to claim 53 wherein the sodium chloride is present in a concentration at or near saturation.

55. A system according to claim 53 wherein the sodium chloride is present in a concentration of up to about 9% weight by volume.

56. A system according to claim 52 wherein the hypertonic solution includes potassium chloride.

57. A system according to claim 43 or 44 or 45 or 46 or 47 or 48 or 49 or 50 or 51 wherein the medium has a resistivity lower than about 150 ohm·cm.

58. A system according to claim 57 wherein the medium has a resistivity lower than about 10 ohm·cm.

59. A system according to claim 57 wherein the medium has a resistivity of about 5 ohm·cm.

60. A system according to claim 43 or 44 or 45 or 46 or 47 or 48 or 49 or 50 or 51 wherein the porous material has an electrical resistivity of at least about 500 ohm·cm.

61. A system according to claim 43 or 44 or 45 or 46 or 47 or 48 or 49 or 50 or 51 wherein the porous material has an electrical resistivity of less than about 500 ohm·cm.

62. A system according to claim 43 or 44 or 45 or 46 or 47 or 48 or 49 or 50 or 51 wherein at least a portion of the wall includes an electrically conductive material.

63. A system according to claim 62 wherein the electrically conductive material of the wall is porous.

64. A system according to claim 62 wherein the electrically conductive material of the wall is nonporous.

65. A system according to claim 62 wherein at least a portion the wall is free of electrically conductive material.

66. A system according to claim 43 or 44 or 45 or 46 or 47 or 48 or 49 or 50 or 51 wherein at least a portion the wall is free of electrically conductive material.

67. A system according to claim 43 or 44 or 45 or 46 or 47 or 48 or 49 or 50 or 51, wherein the wall includes a distal region and a proximal region, and wherein the porous material occupies more of the distal region than the proximal region.

68. A system according to claim 67 wherein at least ⅓rd of the proximal region is free of porous material.

69. A system according to claim 67, wherein the porous material occupies at least ⅓rd of the distal region.

70. A system according to claim 43 or 44 or 45 or 46 or 47 or 48 or 49 or 50 or 51 and further including a radiopaque material carried by the electrode.

71. A system according to claim 43 or 44 or 45 or 46 or 47 or 48 or 49 or 50 or 51 and further including a controller including means for specifying an electrical resistivity for the porous material based, at least in part, upon a desired physiological effect.

72. A system according to claim 44 or 45 or 47 or 48 or 50 or 51 and further including a controller including means for specifying a first electrical resistivity for the porous material to achieve a first tissue lesion characteristic and specifying a second electrical resistivity for the porous material different than the first electrical resistivity to achieve a second tissue lesion characteristic different than the first lesion characteristic.

73. A system according to claim 45 or 48 or 51 and further including a controller for specifying a first electrical resistivity for the porous material to achieve a deep tissue lesion geometry and specifying a second electrical resistivity for the porous material greater than the first electrical resistivity to achieve a shallow tissue lesion geometry.

74. A system according to claim 43 or 44 or 45 or 46 or 47 or 48 or 49 or 50 or 51 and further including a temperature sensing element carried by the electrode, and further including a controller including means for specifying transmission of energy to the medium based, at least in part, upon temperature sensed by the temperature sensing element.

75. A system according to claim 43 or 44 or 45 or 46 or 47 or 48 or 49 or 50 or 51 wherein the porous material is hydrophilic.

76. A system according to claim 46 wherein at least one temperature sensing element is carried by the wall in thermal conductive contact with the exterior of the wall.

77. A system according to claim 46 wherein the porous material comprises a microporous membrane.

78. A system according to claim 46 wherein the porous material comprises an ultrafiltration membrane.

79. A method for heating body tissue comprising the steps of providing a catheter tube having a distal end that carries an electrode comprising a wall having an exterior peripherally surrounding an interior area, an electrically conductive element in the interior area, at least a portion of the wall including an ultraporous material sized to block passage of macromolecules while allowing passage of ions, electrically coupling a source of radio frequency energy to the electrically conductive element to a return electrode in contact with body tissue, guiding the catheter tube into a body, conveying a medium containing ions into the interior area, and ohmically heating body tissue by transmitting radio frequency energy to the electrically conductive element for ionic transport through the medium and ultraporous material to the exterior of the wall for transmission to the return electrode.

80. A method for ablating tissue comprising the steps of providing a catheter tube having a distal end that carries an electrode comprising a wall having an exterior peripherally surrounding an interior area, an electrically conductive element in the interior area, at least a portion of the wall including an ultraporous material sized to block passage of macromolecules while allowing passage of ions, electrically coupling a source of radio frequency energy to the electrically conductive element and to a return electrode in contact with body tissue, guiding the catheter tube into a body, conveying a medium containing ions into the interior area, and ablating tissue by ohmically heating tissue by transmitting radio frequency energy to the electrically conductive element for ionic transport through the medium and ultraporous material to the exterior of the wall for transmission to the return electrode.

81. A method for ablating heart tissue comprising the steps of providing a catheter tube having a distal end that carries an electrode comprising a wall having an exterior peripherally surrounding an interior area, an electrically conductive element in the interior area, at least a portion of the wall including an ultraporous material sized to block passage of macromolecules while allowing passage of ions, electrically coupling a source of radio frequency energy to the electrically conductive element and to a return electrode in contact with body tissue, guiding the catheter tube into a heart chamber, conveying an medium containing ions into the interior area, and ablating heart tissue by ohmically heating heart tissue by transmitting radio frequency energy to the electrically conductive element for ionic transport through the medium and ultraporous material to the exterior of the wall for transmission to the return electrode.

82. A method for heating body tissue comprising the steps of providing a catheter tube having a distal end that carries an electrode comprising a wall having an exterior peripherally surrounding an interior area, an electrically conductive element in the interior area, at least a portion of the wall comprising a porous material sized to pass ions contained in the medium without substantial liquid perfusion through the porous material, electrically coupling a source of radio frequency energy to the electrically conductive element to a return electrode in contact with body tissue, guiding the catheter tube into a body, conveying a medium containing ions into the interior area, and ohmically heating body tissue by transmitting radio frequency energy to the electrically conductive element for ionic transport through the medium and porous material to the exterior of the wall for transmission to the return electrode free of substantial liquid perfusion through the porous material.

83. A method for ablating tissue comprising the steps of providing a catheter tube having a distal end that carries an electrode comprising a wall having an exterior peripherally surrounding an interior area, an electrically conductive element in the interior area, at least a portion of the wall comprising a porous material sized to pass ions contained in the medium without substantial liquid perfusion through the porous material, electrically coupling a source of radio frequency energy to the electrically conductive element and to a return electrode in contact with body tissue, guiding the catheter tube into a body, conveying a medium containing ions into the interior area, and ablating tissue by ohmically heating tissue by transmitting radio frequency energy to the electrically conductive element for ionic transport through the medium and porous material to the exterior of the wall for transmission to the return electrode substantially free of liquid perfusion through the porous material.

84. A method for ablating heart tissue comprising the steps of providing a catheter tube having a distal end that carries an electrode comprising a wall having an exterior peripherally surrounding an interior area, an electrically conductive element in the interior area, at least a portion of the wall comprising a porous material sized to pass ions contained in the medium without substantial liquid perfusion through the porous material, electrically coupling a source of radio frequency energy to the electrically conductive element and to a return electrode in contact with body tissue, guiding the catheter tube into a heart chamber, conveying an medium containing ions into the interior area, and ablating heart tissue by ohmically heating heart tissue by transmitting radio frequency energy to the electrically conductive element for ionic transport through the medium and porous material to the exterior of the wall for transmission to the return electrode substantially free of liquid perfusion through the porous material.

85. A method for heating body tissue comprising the steps of providing a catheter tube having a distal end that carries an electrode comprising a wall having an exterior peripherally surrounding an interior area, an electrically conductive element in the interior area, at least a portion of the wall including a porous material sized to pass ions, the porous material having a bubble point value, electrically coupling a source of radio frequency energy to the electrically conductive element to a return electrode in contact with body tissue, guiding the catheter tube into a body, conveying a medium containing ions into the interior area subject to an internal pressure less than the bubble point value, and ohmically heating body tissue by transmitting radio frequency energy to the electrically conductive element for ionic transport through the medium and porous material to the exterior of the wall for transmission to the return electrode.

86. A method for ablating tissue comprising the steps of providing a catheter tube having a distal end that carries an electrode comprising a wall having an exterior peripherally surrounding an interior area, an electrically conductive element in the interior area, at least a portion of the wall including a porous material sized to pass ions, the porous material having a bubble point value, electrically coupling a source of radio frequency energy to the electrically conductive element and to a return electrode in contact with body tissue, guiding the catheter tube into a body, conveying a medium containing ions into the interior area subject to an internal pressure less than the bubble point value, and ablating tissue by ohmically heating tissue by transmitting radio frequency energy to the electrically conductive element for ionic transport through the medium and porous material to the exterior of the wall for transmission to the return electrode.

87. A method for ablating heart tissue comprising the steps of providing a catheter tube having a distal end that carries an electrode comprising a wall having an exterior peripherally surrounding an interior area, an electrically conductive element in the interior area, at least a portion of the wall including a porous material sized to pass ions, the porous material having a bubble point value, electrically coupling a source of radio frequency energy to the electrically conductive element and to a return electrode in contact with body tissue, guiding the catheter tube into a heart chamber, conveying an medium containing ions into the interior area subject to an internal pressure less than the bubble point value, and ablating heart tissue by ohmically heating heart tissue by transmitting radio frequency energy to the electrically conductive element for ionic transport through the medium and porous material to the exterior of the wall for transmission to the return electrode.

88. A method according to claim 79 or 80 or 81 or 82 or 83 or 84 or 85 or 86 or 87 and further including the step of specifying an electrical resistivity for the porous material based, at least in part, upon a desired physiological effect.

89. A method according to claim 80 or 81 or 83 or 84 or 86 or 87 and further including the step of specifying a first electrical resistivity for the porous material to achieve a first tissue lesion characteristic and specifying a second electrical resistivity for the porous material different than the first electrical resistivity to achieve a second tissue lesion characteristic different than the first lesion characteristic.

90. A method according to claim 80 or 81 or 83 or 84 or 86 or 87 and further including the step of specifying a first electrical resistivity for the porous material to achieve a deep tissue lesion geometry and specifying a second electrical resistivity for the porous material greater than the first electrical resistivity to achieve a shallow tissue lesion geometry.

91. A method according to claim 80 or 81 or 83 or 84 or 86 or 87 and further including the steps of sensing temperature using a sensing element carried by the electrode, and specifying transmission of energy to the medium based, at least in part, upon temperature sensed by the temperature sensing element.

92. A method according to claim 83 further including the steps of providing at least one temperature sensing element that is carried by the wall and in thermal conductive contact with the exterior of the wall, and sensing temperature using the at least one temperature sensing element at least partially during the step of ablating tissue.

* * * * *